United States Patent
Weissman

(10) Patent No.: US 10,076,739 B1
(45) Date of Patent: Sep. 18, 2018

(54) CHEMICAL REACTOR FOR USE WITH OVERLY REACTIVE CHEMICALS

(71) Applicant: Precision Combustion, Inc., North Haven, CT (US)

(72) Inventor: Jeffrey Weissman, Guilford, CT (US)

(73) Assignee: PRECISION COMBUSTION, INC., North Haven, CT (US)

( * ) Notice: Subject to any disclaimer, the term of this patent is extended or adjusted under 35 U.S.C. 154(b) by 393 days.

(21) Appl. No.: 14/801,004

(22) Filed: Jul. 16, 2015

Related U.S. Application Data

(60) Provisional application No. 62/027,299, filed on Jul. 22, 2014.

(51) Int. Cl.
| | |
|---|---|
| *B01J 19/00* | (2006.01) |
| *B01J 19/24* | (2006.01) |
| *C07C 2/84* | (2006.01) |
| *C07C 2/58* | (2006.01) |
| *C07C 29/50* | (2006.01) |

(52) U.S. Cl.
CPC .......... *B01J 19/002* (2013.01); *B01J 19/248* (2013.01); *C07C 2/58* (2013.01); *C07C 2/84* (2013.01); *C07C 29/50* (2013.01); *B01J 2219/00076* (2013.01); *B01J 2219/00245* (2013.01); *B01J 2219/2401* (2013.01); *C07C 2523/34* (2013.01); *C07C 2529/40* (2013.01)

(58) Field of Classification Search
CPC .. C07C 2/58; C07C 2/84; C07C 29/50; C07C 2523/34; C07C 2529/40; B01J 19/002; B01J 19/248; B01J 2219/00076; B01J 2219/00245; B01J 2219/2401
See application file for complete search history.

(56) References Cited

U.S. PATENT DOCUMENTS

| | | | | |
|---|---|---|---|---|
| 3,523,142 | A * | 8/1970 | Child | C07C 2/58 502/231 |
| 3,893,942 | A | 7/1975 | Yang | |
| 4,008,291 | A | 2/1977 | Zabransky | |
| 5,017,731 | A * | 5/1991 | Gesser | C07C 29/50 44/451 |
| 5,276,237 | A * | 1/1994 | Mieville | B01J 12/007 423/418.2 |
| 5,583,240 | A | 12/1996 | Asher | |
| 5,994,567 | A * | 11/1999 | Kingsley | B01F 3/04106 552/208 |
| 6,238,815 | B1 | 5/2001 | Skala | |
| 6,838,064 | B2 | 1/2005 | Sakai | |
| 6,858,768 | B2 * | 2/2005 | Budin | B01J 21/06 585/658 |
| 6,977,064 | B1 | 12/2005 | Adris | |
| 7,279,138 | B2 | 10/2007 | Pagani | |
| 7,550,643 | B2 | 6/2009 | Pfefferle | |
| 7,550,644 | B2 | 6/2009 | Pfefferle | |
| 8,158,074 | B2 | 4/2012 | Filippi | |
| 8,603,407 | B2 | 12/2013 | Pfefferle | |
| 2004/0229752 | A1 | 11/2004 | Long | |
| 2004/0258602 | A1 | 12/2004 | Castaldi | |
| 2005/0166456 | A1 | 8/2005 | Brundage | |
| 2005/0256358 | A1 | 11/2005 | Wang | |
| 2007/0270623 | A1 | 11/2007 | Merrill | |
| 2011/0081291 | A1 | 4/2011 | Baek | |
| 2011/0087056 | A1 * | 4/2011 | Tirtowidjojo | B01J 19/0026 570/175 |
| 2011/0133126 | A1 | 6/2011 | Lippmann | |
| 2011/0150734 | A1 | 6/2011 | Kumakiri | |
| 2012/0216501 | A1 | 8/2012 | Birley | |
| 2012/0258037 | A1 | 10/2012 | Pham | |
| 2013/0233138 | A1 | 9/2013 | Tarozzo | |

FOREIGN PATENT DOCUMENTS

| | | |
|---|---|---|
| CA | 2786353 A1 | 7/2011 |
| CN | 101574636 A | 11/2009 |
| CN | 101792370 A | 8/2010 |
| DE | 102012016561 A1 | 2/2014 |

OTHER PUBLICATIONS

Bruce E. Poling, John M. Prausnitz, and John P. O'Connell, The Properties of Gases and Liquids, 5th Edition, McGraw-Hill, New York, 2001, Chapter 11—"Diffusion Coefficients"; Table of Contents and 11-1-Scope provided.

* cited by examiner

Primary Examiner — Pancham Bakshi
Assistant Examiner — Mark R Luderer
(74) Attorney, Agent, or Firm — Marie F. Zuckerman; Andrew D. Gathy

(57) ABSTRACT

A chemical reactor for use in a chemical process wherein a reactant and/or a target product is prone to produce undesirable byproducts through secondary reactions. The reactor is configured with a first flow passage for passing a flow of an overly reactive reactant; a permeable first wall for controlled flow of the overly reactive reactant into a second flow passage providing a flow of a second reactant; a permeable second wall having a catalyst supported on an inner surface thereof for catalyzing reaction of the reactants flowing in the second flow passage; the permeable second wall passing through a flow containing the target product; and a non-permeable third wall defining a third flow passage for exiting the product mixture. The reactor can be employed in selective oxidation, oxidative dehydrogenation, and alkylation processes to reduce the formation of byproducts.

6 Claims, 18 Drawing Sheets

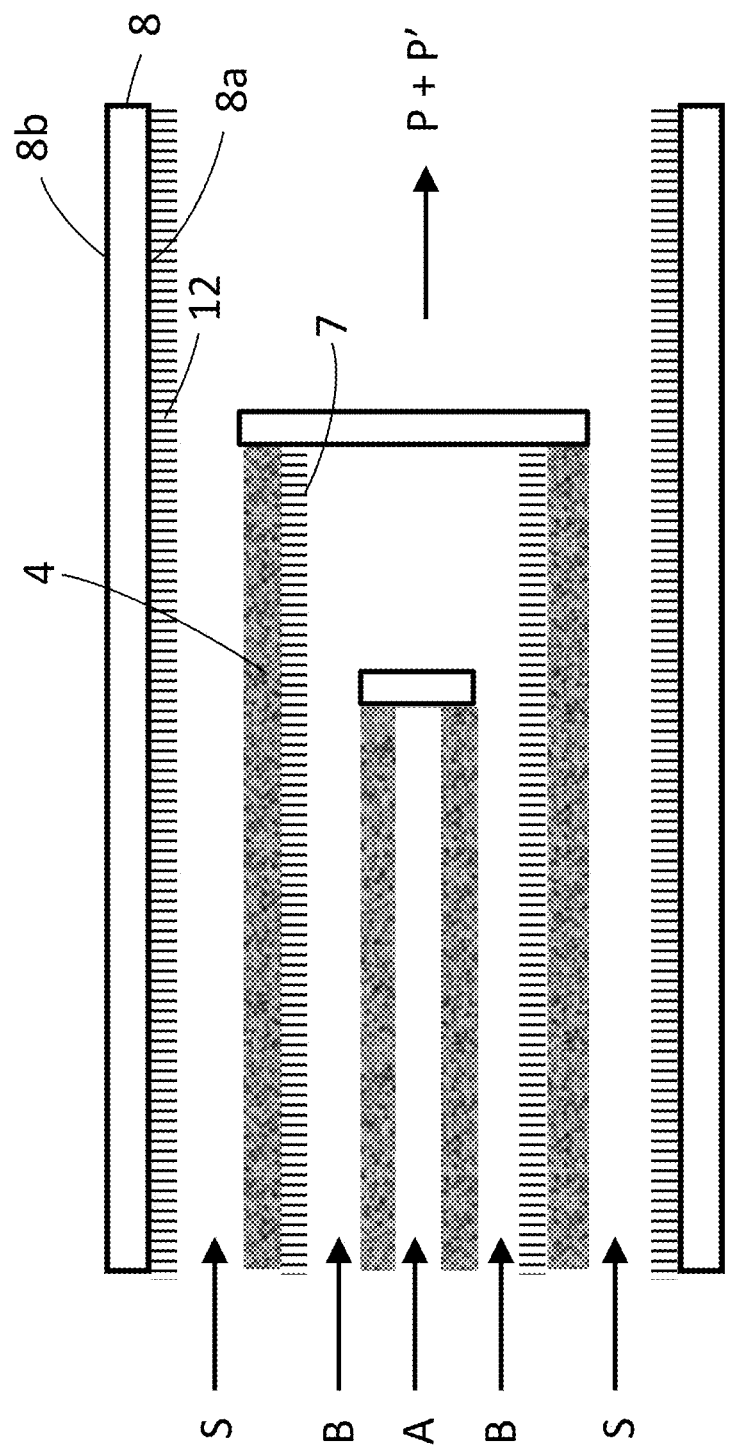

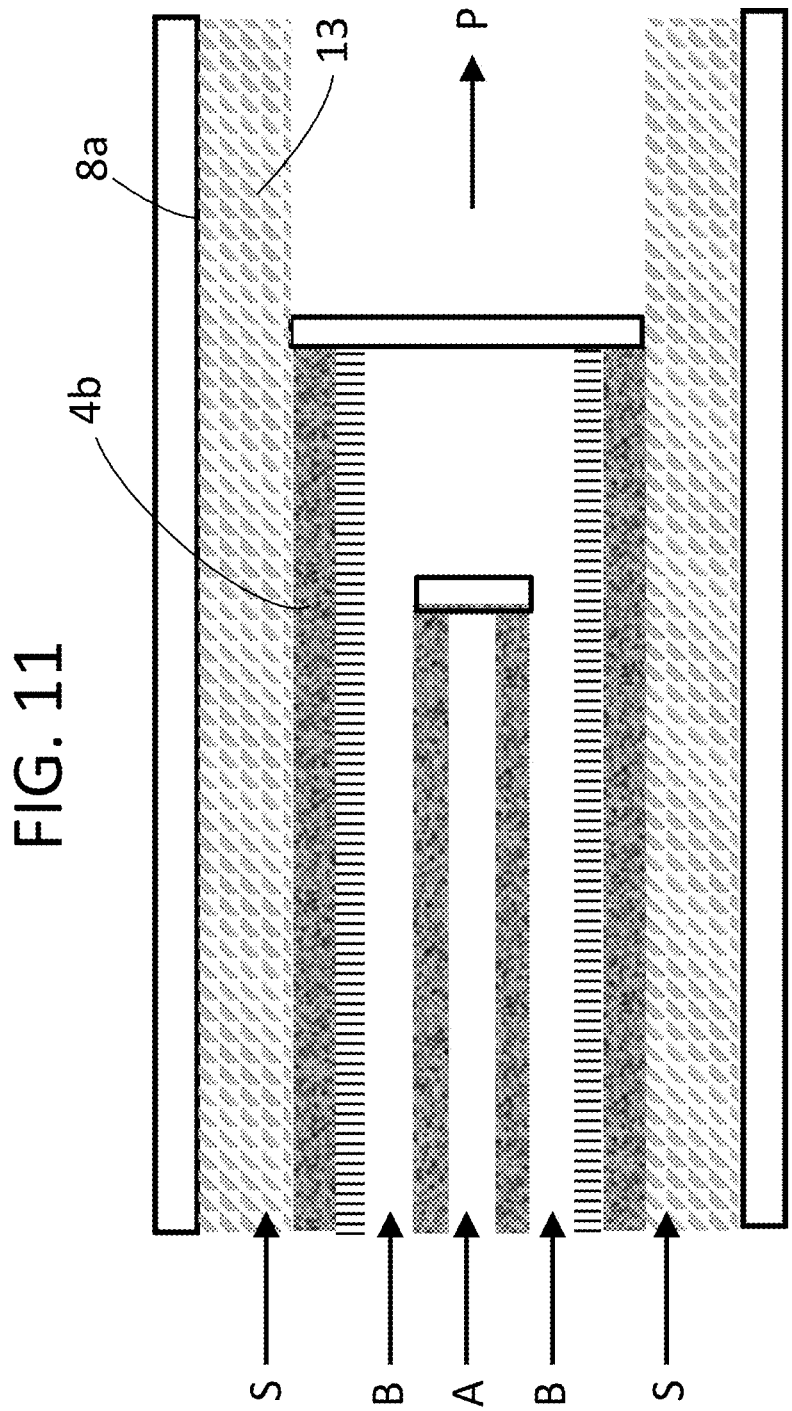

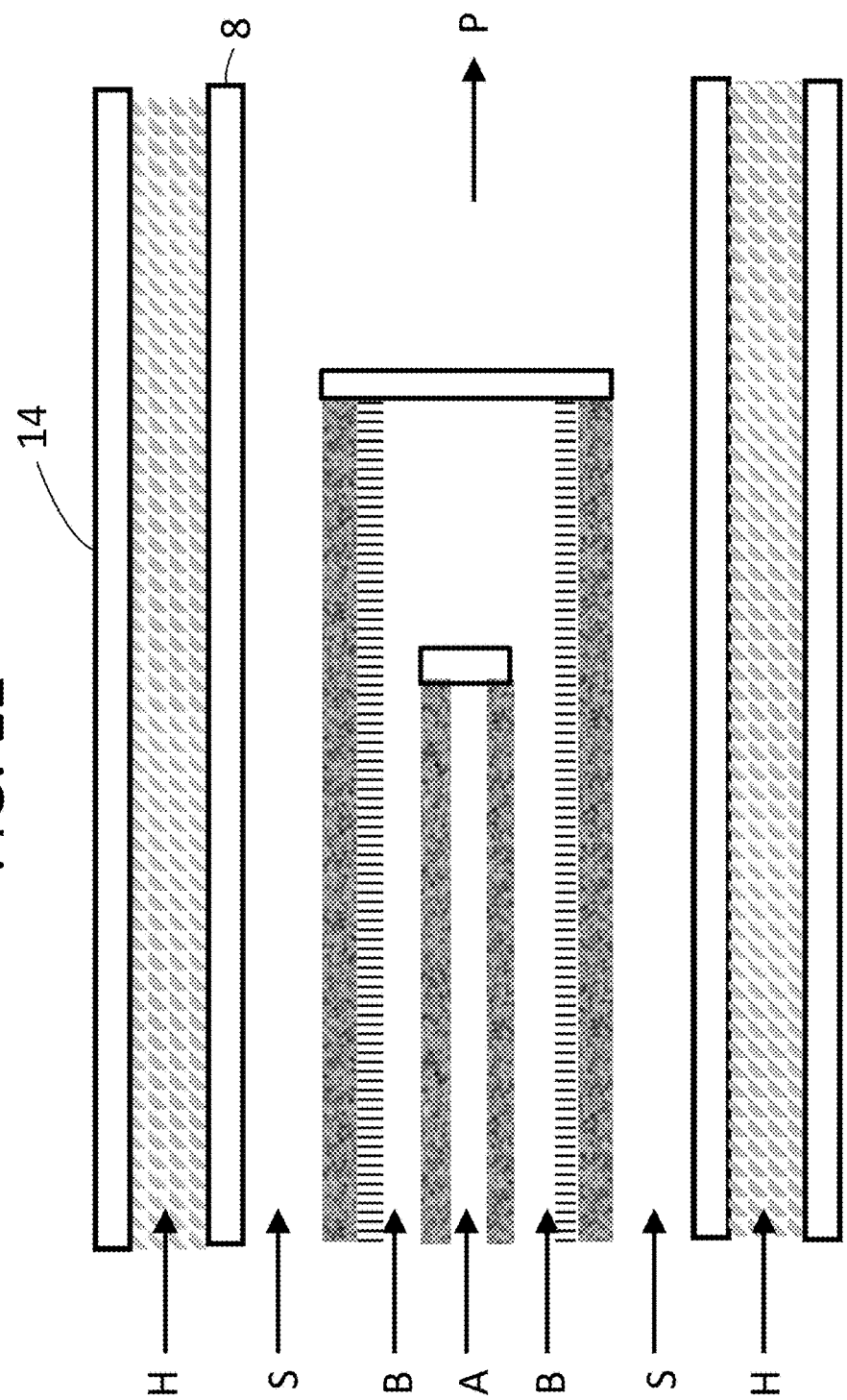

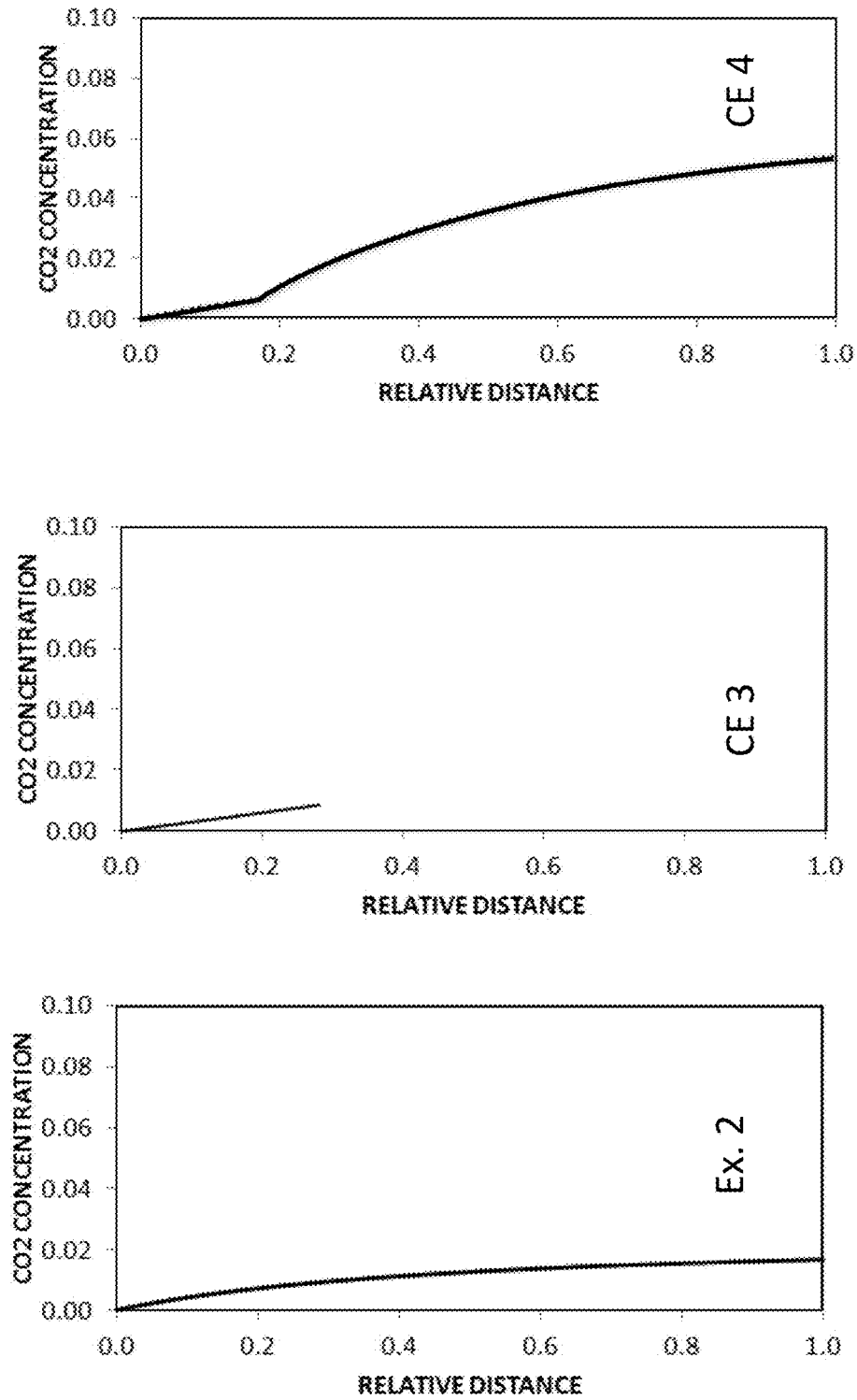

CHEMICAL REACTOR FOR USE WITH OVERLY REACTIVE CHEMICALS

CROSS REFERENCE TO RELATED APPLICATION

This invention claims the benefit of U.S. Provisional Application No. 62/027,299, filed Jul. 22, 2014, the entire contents of which are incorporated herein by reference.

GOVERNMENT RIGHTS

This invention was made with support from the U.S. government under U.S. Contract No. DE-FG02-07ER84846, sponsored by the Department of Energy. The U.S. Government holds certain rights in this invention.

FIELD OF THE INVENTION

The present invention pertains to a chemical reactor for use in converting two or more chemical reactants into at least one chemical product, particularly wherein one of the chemical reactants and/or a desired chemical product is prone to disadvantageous secondary reactions to form one or more undesirable byproducts.

BACKGROUND OF THE INVENTION

Some chemical reactions can be challenging to conduct to high conversion of reactant(s) or high selectivity to a desired product when one of the reactants, or a desired product, or both a reactant and a desired product exhibit a high reactivity to form one or more undesirable byproducts. To overcome this challenge, chemical reactions are often conducted via alternate pathways in order to avoid the overly reactive reactant(s) and/or to avoid a high concentration of desired but reactive product(s). Yet other alternative pathways include using a multiple reaction sequence, as opposed to a one-step or one pot reaction. Often, alternative pathways require complex reactor designs. Yet other alternative pathways operate at low single-pass conversion to less than optimal yield, which then requires recycling and multiple passes to achieve an acceptable yield of desired product(s). All of these alternatives result in large, complex operations that add significantly to the cost of producing the desired product(s).

As an example, in the conversion of methane to methanol, direct selective oxidation is challenging, because one of the reactants, namely oxygen, is overly reactive with methanol. The desired reaction shown in Equation 1, $$CH_4 + \tfrac{1}{2}O_2 \rightarrow CH_3OH \quad (1)$$

is not only exothermic, which has its own difficulties, but is made more difficult, because oxygen reacts with the methane or methanol in secondary reactions to yield undesirable byproducts. Specifically, the reaction of oxygen with methanol can yield complete oxidation byproducts, namely carbon dioxide and water, as shown in Equation (2):

$$CH_3OH + 3/2 O_2 \rightarrow CO_2 + 2H_2O \quad (2)$$

Likewise, over-reaction of oxygen with methane can also lead to complete oxidation byproducts, as shown in Equation (3):

$$CH_4 + 2O_2 \rightarrow CO_2 + 2H_2O \quad (3)$$

Either way, the outcome includes excessive production of undesired products $CO_2$ and $H_2O$ and generation of heat, which accelerates the rate of the undesired reactions resulting in large amounts of methane not being converted to methanol. Conventional fixed-bed reactors avoid some of these undesired reactions by operating at very low conversions, therefore requiring excessively large reactor volumes and recycle volumes in order to achieve a high yield of methanol. Generally, such processes are not commercially desirable.

Alternatively, industrial practice involves a first reaction step of converting methane to synthesis gas (hereinafter "syn-gas"), that is, a mixture of carbon monoxide (CO) and hydrogen ($H_2$) by way of methane-steam reforming; followed by a second reaction step in which syngas is converted to methanol. This process, due to its highly endothermic first step, requires large reactors in order to reach economy of scales and also requires complex engineering and operations due to a requirement for large energy input. In view of the above, it would be desirable to discover a one-step methane to methanol process that operates at low temperatures and high yields of methanol while avoiding undesirable secondary reactions. More generally, other reactions of interest include direct one-step selective or partial oxidation of alkanes, alkenes, or aromatic hydrocarbons, whether linear, branched, or cyclic, to the corresponding alcohols. For example, butane-to-butanol and benzene-to-phenol are also of interest.

Another example involves the oxidative dehydrogenation of alkanes to alkenes, for example, the oxidative dehydrogenation of methane to form ethylene, according to Equation (4):

$$2CH_4 + O_2 \rightarrow C_2H_4 + 2H_2O \quad (4)$$

In this example oxygen is the overly reactive component. Ethylene is more valued as compared to the starting methane. Yield of ethylene is negatively impacted by undesired reaction of product ethylene with reactant oxygen, Equation (5), and overreaction of reactants methane and oxygen, Equation (6), resulting in this oxidative process being of limited commercial application for the reason that methane and ethylene react disadvantageously with oxygen to form complete oxidation byproducts.

$$C_2H_4 + 3O_2 \rightarrow 2CO_2 + 2H_2O \quad (5)$$

$$CH_4 + 2O_2 \rightarrow CO_2 + 2H_2O \quad (6)$$

Yet another example involves alkylation of isobutane with butylene (an olefin) to form isooctane, a high octane low emissions component of gasoline. Alkylation proceeds according to Equation (7):

$$i\text{-}C_4H_{10} + C_4H_8 \rightarrow i\text{-}C_8H_{18} \quad (7)$$

wherein the isooctane product comprises a mixture of any number of 5, 6, or 7 carbon-chain isomers, with 3, 2, or 1 attached methyl ($-CH_3$) groups, respectively. The butylene olefin is the overly reactive component. Undesired reaction can occur between the butylene olefin and isooctane product according to Equation (8):

$$i\text{-}C_8H_{18} + C_4H_8 \rightarrow i\text{-}C_{12}H_{26} \quad (8)$$

with higher polymerization another possibility as shown, for example, in Equation (9):

$$i\text{-}C_{12}H_{26} + C_4H_8 \rightarrow i\text{-}C_{16}H_{34} \quad (9)$$

Moreover, undesired side reactions can occur in the polymerization of butylene with itself; for example, the dimerization of butylene is shown in Equation (10):

$$2C_4H_8 \rightarrow C_8H_{16} \quad (10)$$

Given the aforementioned difficulties, the alkylation of isobutane with butylene is conducted commercially using a homogeneous liquid acid catalyst, either liquid sulfuric acid or hydrofluoric acid. In either case, the acid needs to be blended with the reactants, separated from the products, and cleaned before reuse. Moreover, make-up acid must be added to replace acid that was consumed. While this liquid acid process is practiced on a large scale, it presents unique challenges due to a need to refrigerate the reactors in order to prevent thermal run-away reactions and a need to handle large volumes of corrosive and hazardous acids. Recently some solid-acid alternatives have been proposed to replace the homogeneous liquid acid catalyst; but here too, olefin polymerization side reactions can block catalytically active sites in the solid-acid catalyst. To overcome these issues, especially those related to catalyst deactivation, a combination of expensive and complex catalyst formulations and complex reactor designs is required in order to allow for frequent or continuous catalyst regeneration.

The difficulties and disadvantages of the aforementioned examples can be found in other specific chemical reactions also characterized by an overly reactive reactant, an overly reactive product, or both overly reactive reactant and overly reactive product, which participate in secondary reactions to form undesirable byproducts.

FIG. 1 illustrates a conventional prior art fixed-bed reactor wherein a single tubular reactor filled with solid catalyst particles has an inlet at one end for feeding a reactant mixture (A+B) and an outlet at an opposite end for exiting a product mixture (P). In circumstances wherein one reactant or one product is overly reactive towards secondary reactions, a concentration of undesirable byproducts accumulates along the length of the reactor.

FIG. 2 illustrates another prior art reactor, as described for example in U.S. Pat. No. 7,550,644, wherein an overly reactive reactant, A, flows through an inner tube that terminates in a catalytic zone of larger diameter; while reactant B enters the catalytic zone via a separate inlet. Reactants A and B mix in the catalytic zone and react on the surface of a catalyst coating the inner wall of the catalytic zone to form product P. This apparatus likewise leads to an accumulation of undesirable byproducts along the length of the catalytic zone, resulting from secondary reactions of overly reactive reactant A or product P.

U.S. Pat. No. 6,977,064, as illustrated in FIG. 3, describes a reactor comprising two concentric tubes such that the inner tube is constructed of a permeable material and the outer tube is constructed of a non-permeable material; and the annular space between the inner and outer tubes is filled with a particulate catalyst. A high reactivity reactant, A, is fed into the inner tube and passes at a controlled rate through the permeable material into the catalytic annular region, where it contacts a flow of reactant B to produce product P. The reactor provides for catalytic reaction through the entire annular region, which leads to an accumulation of undesirable byproducts along the length of the reactor resulting from secondary reactions of overly reactive reactant A or product P.

Finally, FIG. 4 illustrates another prior art reactor, as described in U.S. 2008/0234528A1, now U.S. Pat. No. 8,603,407, wherein two concentric tubes are provided such that the inner tube is constructed of a permeable material and the outer tube is constructed of a non-permeable material; and the annular space between the inner and outer tubes is hollow or empty space. Here, a catalyst is coated onto the inner surface of the outer tube, rather than being provided as particulates filling the annular space. The overly reactive reactant, A, is fed into the inner tube and passes at a controlled rate through the permeable material into the annular region, where it diffuses through a flow of reactant B towards the catalyst coating on the inner surface of the outer tube. Such an apparatus provides for reaction at the catalyst surface along the length of the outer tube, which can lead to an accumulation of undesirable byproducts resulting from secondary reactions of high reactivity reactant A or desired product P.

In view of the above, a need exists in the art for a reactor that reduces secondary reactions of one or more overly reactive reactants, or one or more overly reactive products, or an overly reactive reactant and an overly reactive product. Such a reactor would find use in providing a higher yield of desirable product(s) in circumstances wherein one or more reactants and/or one or more products are overly reactive via secondary reactions to form undesirable byproducts.

SUMMARY OF THE INVENTION

In one aspect, this invention provides a chemical reactor for converting two or more chemical reactants into at least one chemical product, wherein the reactor comprises:
(a) a first flow passage fluidly connected to at least one inlet;
(b) a first permeable wall characterized by an inner surface and an outer surface and a plurality of pores extending from the inner surface to the outer surface; the first permeable wall extending along at least a portion of length of the first flow passage; the inner surface of the first permeable wall being fluidly connected to the first flow passage;
(c) a second flow passage extending along the length of the first permeable wall; the second flow passage being fluidly connected to the outer surface of the first permeable wall;
(d) a second permeable wall characterized by an inner surface and an outer surface and a plurality of pores extending from the inner surface to the outer surface; the second permeable wall extending along the length of the second flow passage; the second permeable wall supporting on its inner surface a catalyst; the inner surface of the second permeable wall including the catalyst being fluidly connected to the second flow passage;
(e) a third flow passage extending at least along the length of the second permeable wall; the third flow passage being fluidly connected to the outer surface of the second permeable wall;
(f) a non-permeable wall characterized by an inner surface and an outer surface; the non-permeable wall extending along the length of the third flow passage; the inner surface of the non-permeable wall being fluidly connected to the third flow passage; and
(g) an outlet fluidly connected to the third flow passage.

In another aspect this invention provides for a process of forming a target chemical product with reduced formation of undesirable byproducts, the process comprising:
(a) feeding a first reactant through a first inlet into a first flow passage;
(b) passing the first reactant in the first flow passage through a first permeable wall into a second flow passage; the first permeable wall characterized by an inner surface and an outer surface and a plurality of pores extending from the inner surface to the outer surface thereof; the first permeable wall extending along at least a portion of length of the first flow passage; the inner surface of the first permeable wall being fluidly connected to the first flow passage;

(c) feeding a second reactant through a second inlet into the second flow passage extending along the length of the first permeable wall; the second flow passage being fluidly connected to the outer surface of the first permeable wall; wherein the first and second reactants mix within the second flow passage;

(d) contacting the mixture of the first and second reactants on a catalyst supported on an inner surface of a second permeable wall, the contacting conducted under process conditions sufficient to form the target chemical product; the second permeable wall characterized by the inner surface and an outer surface and a plurality of pores extending from the inner surface to the outer surface thereof; the second permeable wall extending along the length of the second flow passage and being fluidly connected to the second flow passage;

(e) passing the target product and any unconverted first and second reactants through the second permeable wall into a third flow passage extending at least along the length of the second permeable wall; the third flow passage being defined by the outer surface of the second permeable wall and a non-permeable third wall;

(f) exiting the target product and any unconverted first and second reactants through an outlet connected to the third flow passage.

The reactor and process of this invention find utility in chemical reactions wherein at least one reactant, or at least one product, or at least one reactant and one product are overly reactive, in the sense that said overly reactive reactant and/or product is prone to disadvantageous secondary reaction(s) to form one or more undesirable byproducts. Beneficially, the reactor and process of this invention reduce secondary reactions of the overly reactive reactant(s) and/or the overly reactive product(s), thereby providing a higher yield of desirable target reaction product and a lower yield of undesirable byproducts.

DRAWINGS

FIG. 1 depicts a longitudinal cross-sectional view of a prior art fixed bed reactor.

FIG. 2 depicts a longitudinal cross-sectional view of a prior art reactor as described in U.S. Pat. No. 7,550,644.

FIG. 3 depicts a longitudinal cross-sectional view of a prior art reactor as described in U.S. Pat. No. 6,977,064.

FIG. 4. depicts a longitudinal cross-sectional view of a prior art reactor as described in U.S. 2008/0234528A1.

FIG. 10 depicts a longitudinal cross-sectional view of a fifth embodiment of a reactor of this invention.

FIG. 11 depicts a longitudinal cross-sectional view of a sixth embodiment of a reactor of this invention.

FIG. 12 depicts a longitudinal cross-sectional view of a seventh embodiment of a reactor of this invention.

Figure 5:
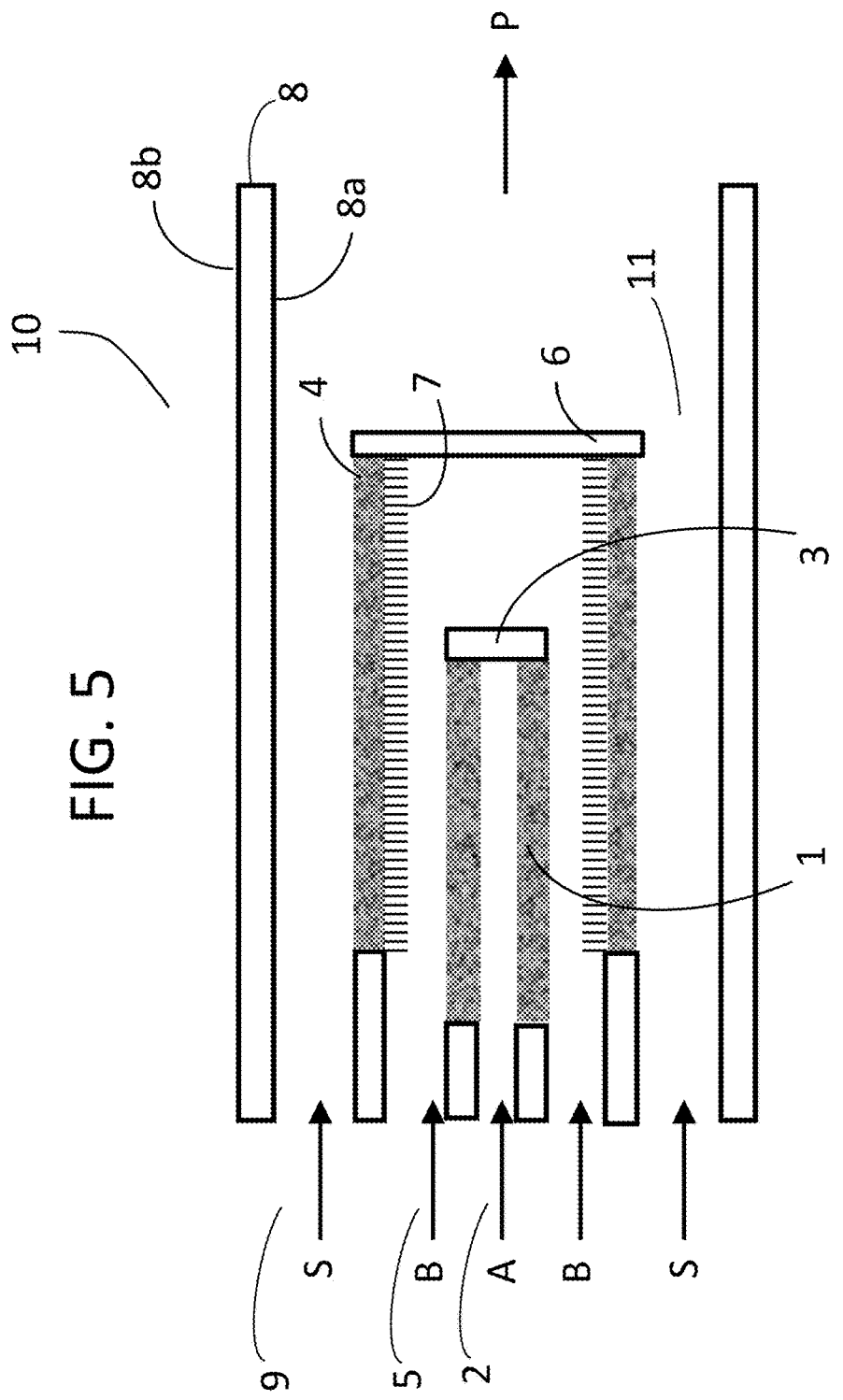
FIG. 5 depicts a longitudinal cross-sectional view of a first embodiment of a chemical reactor of this invention.
Figure 17:
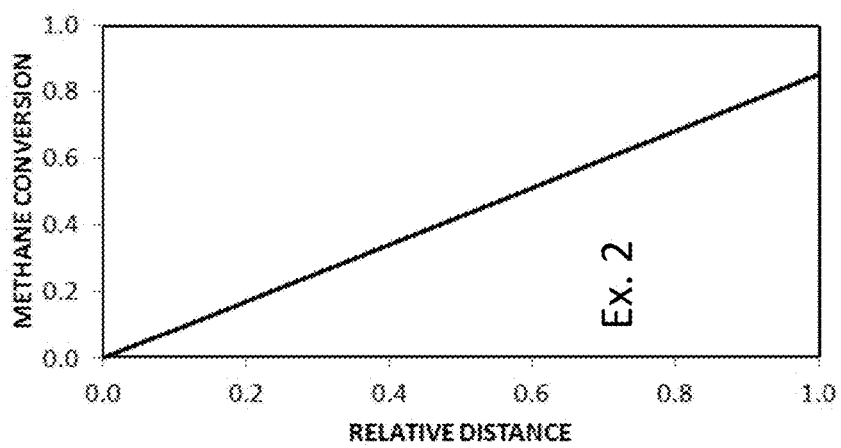

FIG. 17 presents a graph plotting methane conversion as a function of relative distance along the length of a reactor of this invention as illustrated in FIG. 5, as employed in the oxidation of methane with oxygen to form methanol.

Figure 1:
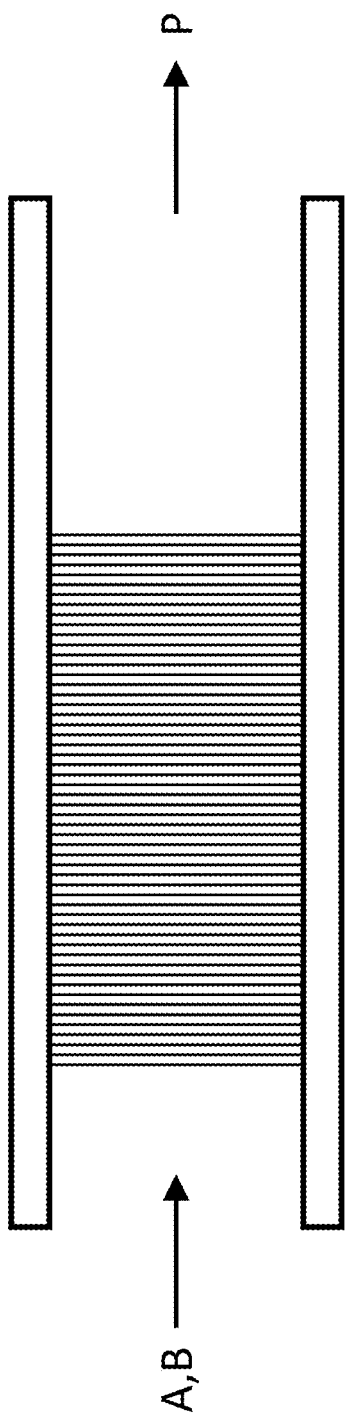
Figure 2:
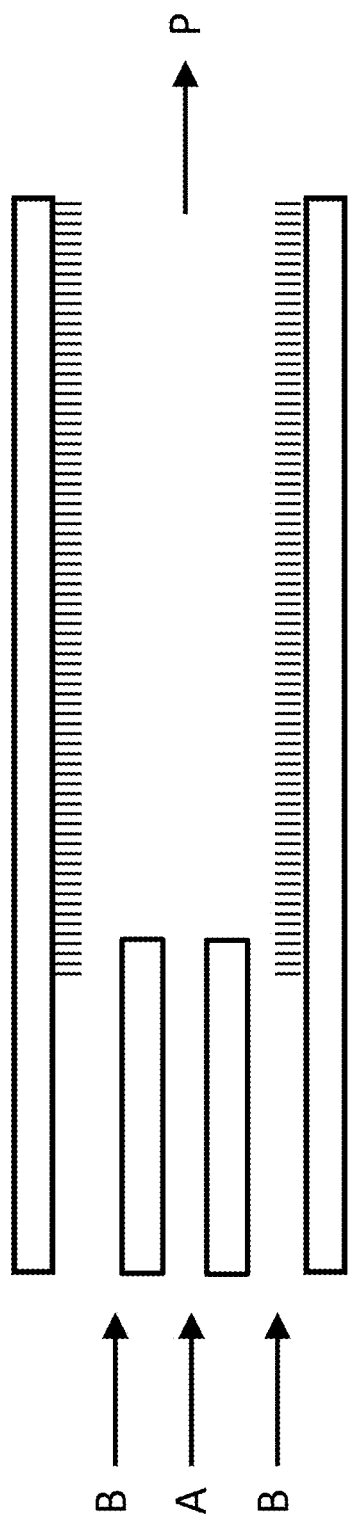
Figure 3:
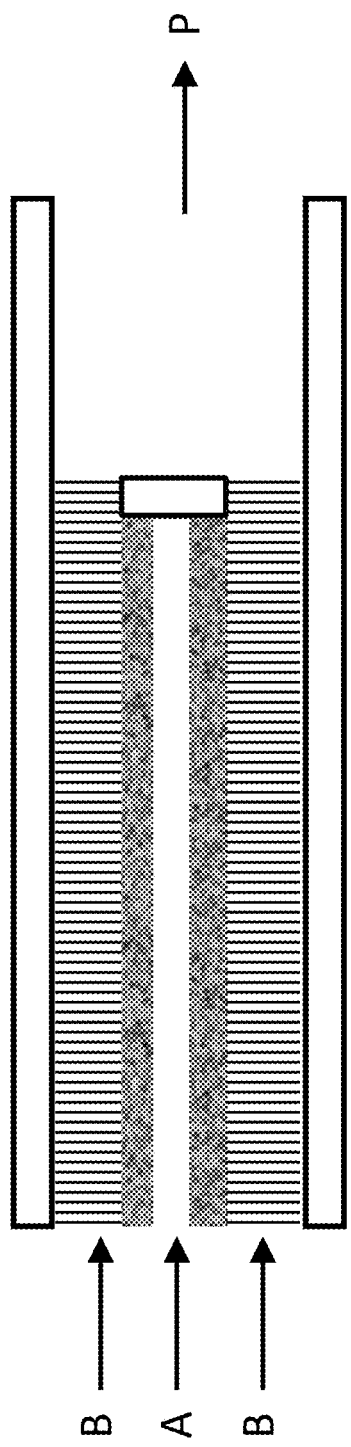
Figure 18:
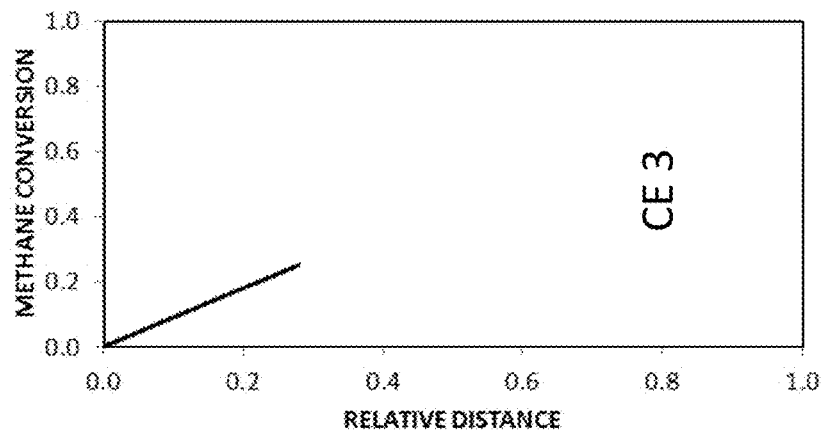

FIG. 18 presents a graph plotting methane conversion as a function of relative distance along the length of a comparative prior art reactor, as illustrated in FIG. 1.

Figure 4:
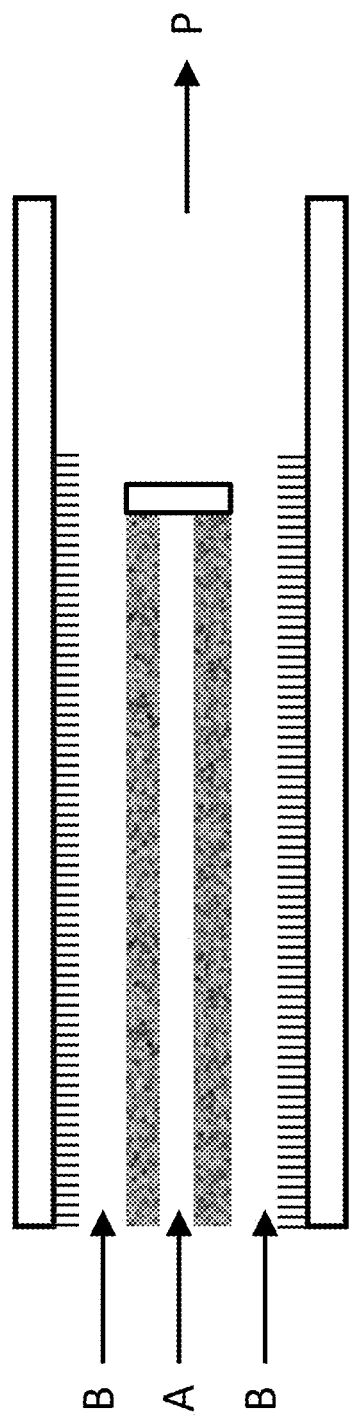
Figure 19:
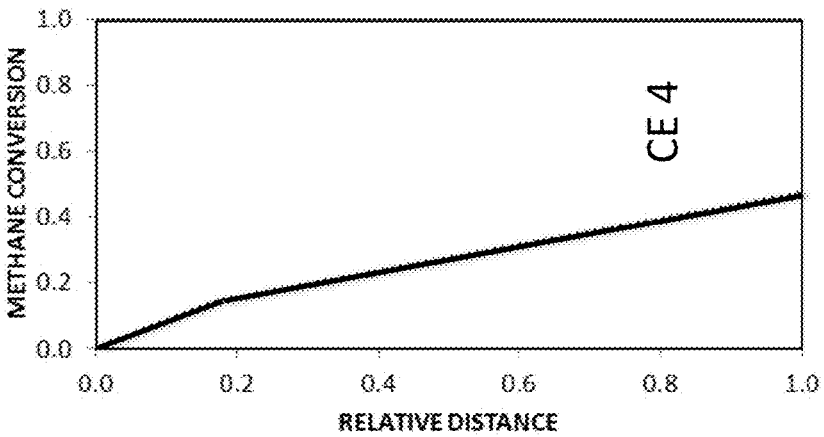

FIG. 19 presents a graph plotting methane conversion as a function of relative distance along the length of a comparative prior art reactor, as illustrated in FIG. 4.

Figure 20:
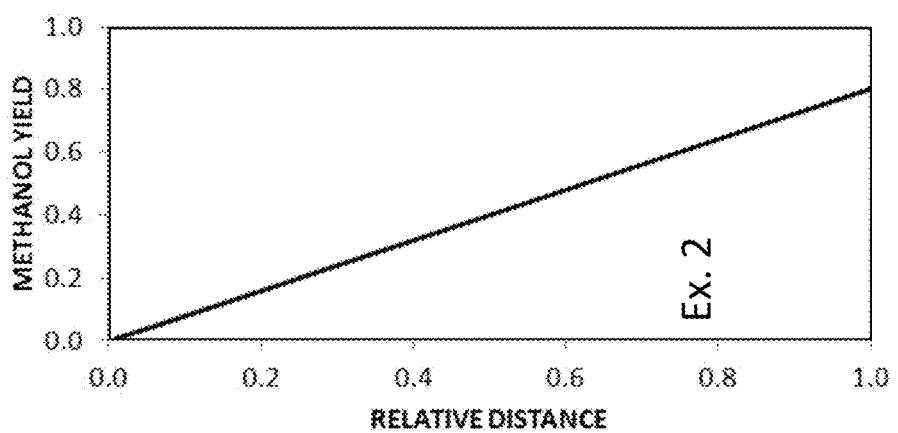

FIG. 20 presents a graph plotting methanol yield as a function of relative distance along the length of a reactor of this invention as illustrated in FIG. 5, as employed in the oxidation of methane with oxygen to form methanol.

Figure 21:
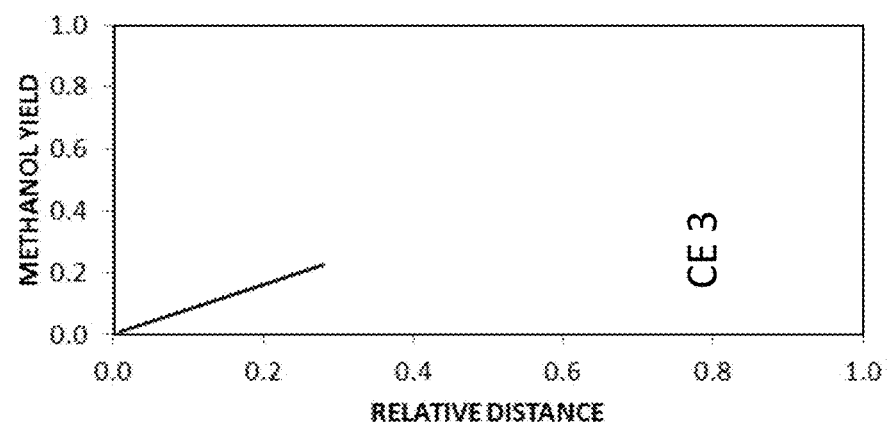

FIG. 21 presents a graph plotting methanol yield as a function of relative distance along the length of a comparative prior art reactor, as illustrated in FIG. 1.

Figure 22:
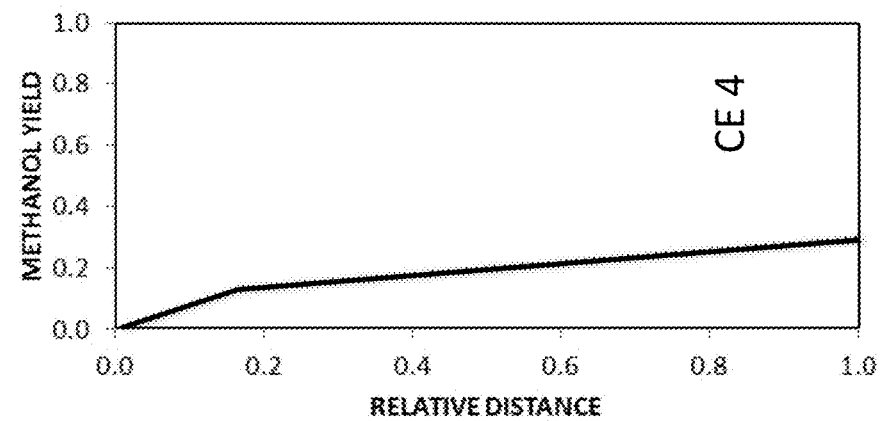

FIG. 22 presents a graph plotting methanol yield as a function of relative distance along the length of a comparative prior art reactor, as illustrated in FIG. 4.

FIG. 23 presents a graph plotting carbon dioxide concentration in a product stream as a function of relative distance along the length of a reactor of this invention as illustrated in FIG. 5, as employed in the oxidation of methane with oxygen to form methanol.

FIG. 24 presents a graph plotting carbon dioxide concentration in a product stream as a function of relative distance along the length of a comparative prior art reactor, as illustrated in FIG. 1.

FIG. 25 presents a graph plotting carbon dioxide concentration in a product stream as a function of relative distance along the length of a comparative prior art reactor, as illustrated in FIG. 4.

Figure 26:
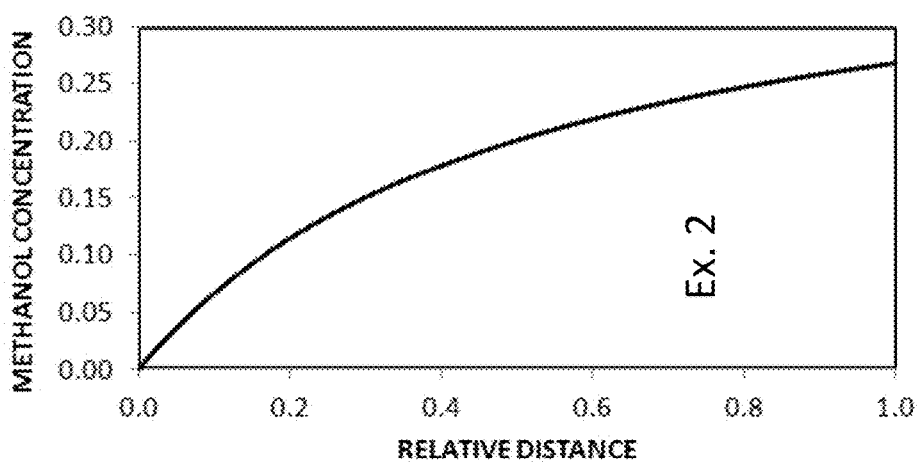

FIG. 26 presents a graph plotting methanol concentration in a product stream as a function of relative distance along the length of a reactor of this invention as illustrated in FIG. 5, as employed in the oxidation of methane with oxygen to form methanol.

Figure 27:
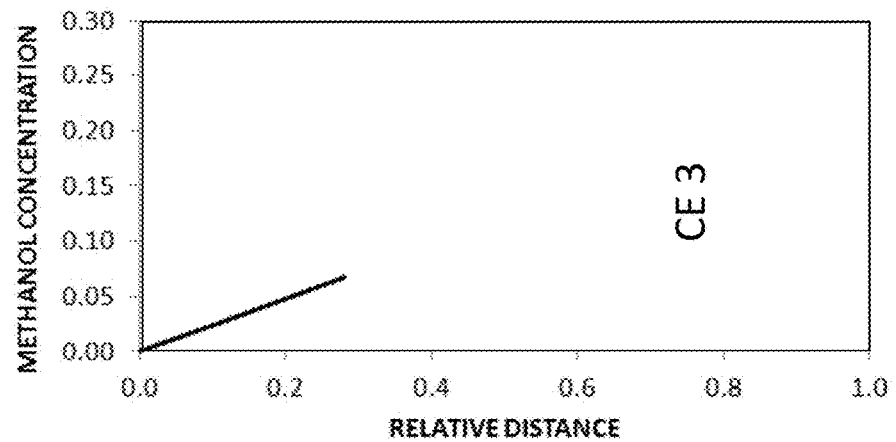

FIG. 27 presents a graph plotting methanol concentration in a product stream as a function of relative distance along the length of a comparative prior art reactor, as illustrated in FIG. 1.

Figure 28:
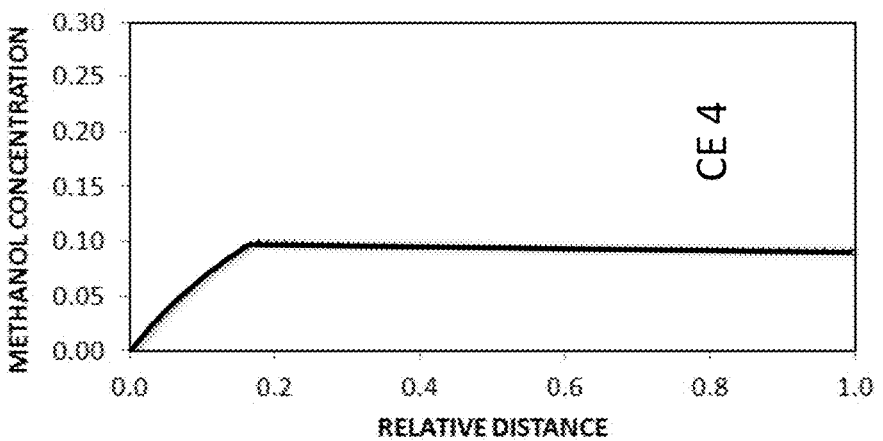

FIG. 28 presents a graph plotting methanol concentration in a product stream as a function of relative distance along the length of a comparative prior art reactor, as illustrated in FIG. 4.

DETAILED DESCRIPTION OF THE INVENTION

For purposes of clarity, the following terms are defined.
The term "fluid" refers to a substance in a gas, liquid, or super-critical state of matter including any substance that requires containment or conforms to the shape of a bounding container. The term "flow" refers to movement of the fluid when acted upon by a force, such as gravity, a pressure gradient, or other external action.

The term "permeable" refers to an ability of a material to pass fluids, namely gases, liquids, and supercritical matter, through the material from an inlet side to an outlet side. The term is intended to include (a) non-selective passage wherein all components of a fluid mixture pass through the material without discrimination; and (b) selective passage wherein one or a few, but not all, of the components of a fluid mixture pass through the material.

The words "non-permeable" or "having no measurable degree of permeability" mean that essentially no detectable amount of any fluid passes through a material, or alternatively, that any amount of fluid that passes through a material has essentially no measurable impact on the behavior of a system or a process using that material, for example, in terms of thermal behavior and/or effects on reactivity, selectivity, yield, and conversion of reactants or products. Thus, some negligible transport of fluid or fluid components through a non-permeable material is permitted provided the extent of transport does not detectably impact on a downstream process.

The term "porous" refers specifically to non-selective passage of all components of a fluid through a substance.

The term "pore" or "pores" refers, respectively, to one or more holes or channels that extend from one surface of a material to another surface of the material, e.g., from an inner surface to an outer surface. The pore structure may provide for a uniform injection of fluid along the length of a permeable surface. Such permeable materials will be characterized by closely spaced holes or pores or passages there through, on the order of nanometers or tenths of microns apart. The cross-sectional shape of the pores or channels is not particularly critical. The pores or channels, for example, may have a circular, elliptical, triangular, square, rectangular, hexagonal, octahedral or even irregular cross-section, or any other suitable cross-sectional shape. The critical dimension of the pores or channels may range from about 10 Angstroms (1 nanometer, nm) to about 100,000 Angstroms (10,000 nm or 10 microns). Preferred are pores ranging from about 0.05 micron to about 10 microns. A range of percent porosity from about 20 to 60 percent is preferred, wherein percent porosity is a measure of the open space afforded by the pores and is defined as 100 percent minus part density [i.e., 100−(100×apparent density/solid density)]. More preferred is a percent porosity of from about 30 to 45 percent. Means for creating porosity in structures are well known in the art; examples include sintering of particles to yield a non-fully dense shaped object, laser drilling, chemical etching, and photolithographic etching. Alternatively, the permeable material may have a porosity that provides for a non-uniform injection of fluid along the length of the permeable surface, provided that the average pore diameter and percent porosity of the porous material remain within the scope defined hereinabove.

The term "controlled flow rate" is defined as a rate of flow in which the actual measured rate corresponds essentially to the desired rate, in terms of quantity of mass or moles of a component of a fluid or all of the components of a fluid, as measured over a fixed time interval through a defined surface, e.g. $g/s/cm^2$ or $mol/hr/m^2$. Furthermore, the term "uniform flow rate" corresponds to a situation in which there is little to no deviation in the flow rate passing through a defined surface regardless of the location on that defined surface.

Thus in one aspect, this invention provides for a chemical reactor for use in forming at least one target chemical product with reduced formation of undesirable byproducts, comprising:
(a) a first flow passage fluidly connected to at least one inlet;
(b) a first permeable tube characterized by an inner surface and an outer surface and a plurality of pores extending from the inner surface to the outer surface; the first permeable tube extending along at least a portion of length of the first flow passage; the inner surface of the first permeable tube being fluidly connected to the first flow passage;
(c) a second flow passage extending along the length of the first permeable tube; the second flow passage being fluidly connected to the outer surface of the first permeable tube;
(d) a second permeable tube characterized by an inner surface and an outer surface and a plurality of pores extending from the inner surface to the outer surface; the second permeable tube extending along the length of the second flow passage and arranged circumferentially around the first permeable tube; the second permeable tube supporting on its inner surface a catalyst coating; the inner surface of the second permeable tube including the catalyst coating being fluidly connected to the second flow passage such that the second flow passage comprises the annular space between the first and second permeable tubes;
(e) a third flow passage extending at least along the length of the second permeable tube; the third flow passage being fluidly connected to the outer surface of the second permeable tube;
(f) a non-permeable tube characterized by an inner surface and an outer surface; the non-permeable tube arranged circumferentially around the second permeable tube and extending along the length of the third flow passage; the inner surface of the non-permeable tube being fluidly connected to the third flow passage such that the third flow passage comprises the annular space between the second permeable tube and the non-permeable tube; and
(g) an outlet fluidly connected to the third flow passage.

In another aspect, this invention provides for a process of forming a target chemical product with reduced formation of undesirable byproducts, the process comprising:
(a) feeding a first reactant through a first inlet into a first flow passage;
(b) passing the first reactant in the first flow passage through a first permeable tube into a second flow passage; the first permeable tube characterized by an inner surface and an outer surface and a plurality of pores extending from the inner surface to the outer surface thereof; the first permeable tube extending along at least a portion of length of the first flow passage; the inner surface of the first permeable tube being fluidly connected to the first flow passage;
(c) feeding a second reactant through a second inlet into the second flow passage extending along the length of the first permeable tube; the second flow passage being fluidly connected to the outer surface of the first permeable tube; wherein the first and second reactants mix within the second flow passage;
(d) contacting the mixture of the first and second reactants on a catalyst coating supported on an inner surface of a second permeable tube, the contacting conducted under process conditions sufficient to form the target chemical product; the second permeable tube characterized by the inner surface and an outer surface and a plurality of pores extending from the inner surface to the outer surface thereof; the second permeable tube extending along the length of the second flow passage and being fluidly connected to the second flow passage;

(e) passing the target product and any unconverted first and second reactants through the second permeable tube into a third flow passage extending at least along the length of the second permeable tube; the third flow passage being fluidly connected to the outer surface of the second permeable tube and fluidly connected to a non-permeable third tube;

(f) exiting the target product and any unconverted first and second reactants through an outlet connected to the third flow passage.

In one embodiment, a process is provided for selective oxidation of a hydrocarbon, preferably, a $C_{1-10}$ hydrocarbon, to produce a corresponding alcohol, preferably, a $C_{1-10}$ alcohol. The process comprises contacting the hydrocarbon with an oxidant in the presence of a catalyst in the above-described chemical reactor of this invention, the contacting occurring under reaction conditions sufficient to produce the corresponding alcohol; wherein the oxidant is fed into the first flow passage of said reactor, and the hydrocarbon is fed into the second flow passage of said reactor; and reaction of the hydrocarbon and oxidant occurs on a catalyst supported on the inner surface of the second permeable wall of said reactor. This embodiment is illustrated in the selective catalytic oxidation of methane with oxygen to form methanol.

In another embodiment, a process is provided for selective oxidative dehydrogenation of an alkane, preferably, a $C_{1-8}$ alkane, to produce an alkene, preferably, a $C_{2-9}$ alkene, comprising contacting the alkane with an oxidant in the presence of a catalyst in the above-described reactor of this invention, the contacting occurring under reaction conditions sufficient to produce the alkene; wherein the oxidant is fed into the first flow passage of said reactor, and the alkane is fed into the second flow passage of said reactor; and the reaction of the alkane with the oxidant occurs on a catalyst supported on the inner surface of the second permeable wall of said reactor. This embodiment is preferably illustrated in the oxidative dehydrogenation of methane to form ethylene.

In yet another embodiment, a process is provided for the alkylation of an alkane to produce the corresponding alkylated alkane, comprising contacting the alkane, preferably, a $C_{2-10}$ alkane, with an olefin, preferably, a $C_{2-6}$ olefin, in the presence of a catalyst in the above-described reactor of this invention, the contacting occurring under reaction conditions sufficient to produce the alkylated alkane; wherein the olefin is fed into the first flow passage of said reactor, and the alkane is fed into the second flow passage of said reactor, and the reaction of the alkane and olefin occur at the catalyst supported on the inner surface of the second permeable wall of said reactor. This embodiment is preferably illustrated in the catalytic alkylation of isobutane with butylene to form isooctane.

In contrast to the prior art discussed hereinabove and illustrated in FIGS. 1-4, this invention provides for a reactor apparatus useful in producing an acceptable, preferably, a high yield of target chemical product(s) while limiting secondary reactions to undesirable byproducts. While the apparatus of this invention can be adapted to many distinct embodiments including a nest of tubes, or a layered set of plates, or a bundle of micro-reactors, the invention is most easily envisioned as a nest of tubes. Even within the tubular reactor concept, the tubes are not necessarily limited to a concentric arrangement of rectilinear cylinders having a circular cross-section. In fact, besides a circular cross-section, the tubes can have an elliptical, triangular, rectangular, or other cross-sectional shape. Likewise, the tubes can have a curvature other than cylindrical; and their longitudinal axes can be offset rather than coaxial. Other embodiments are possible that the skilled person will recognize as falling within the scope of the invention. For simplicity, the description henceforth will focus on a reactor comprising a concentric and coaxial arraignment of cylindrical tubes having a circular radial cross-section; but the invention is not limited thereto.

Figure 6:
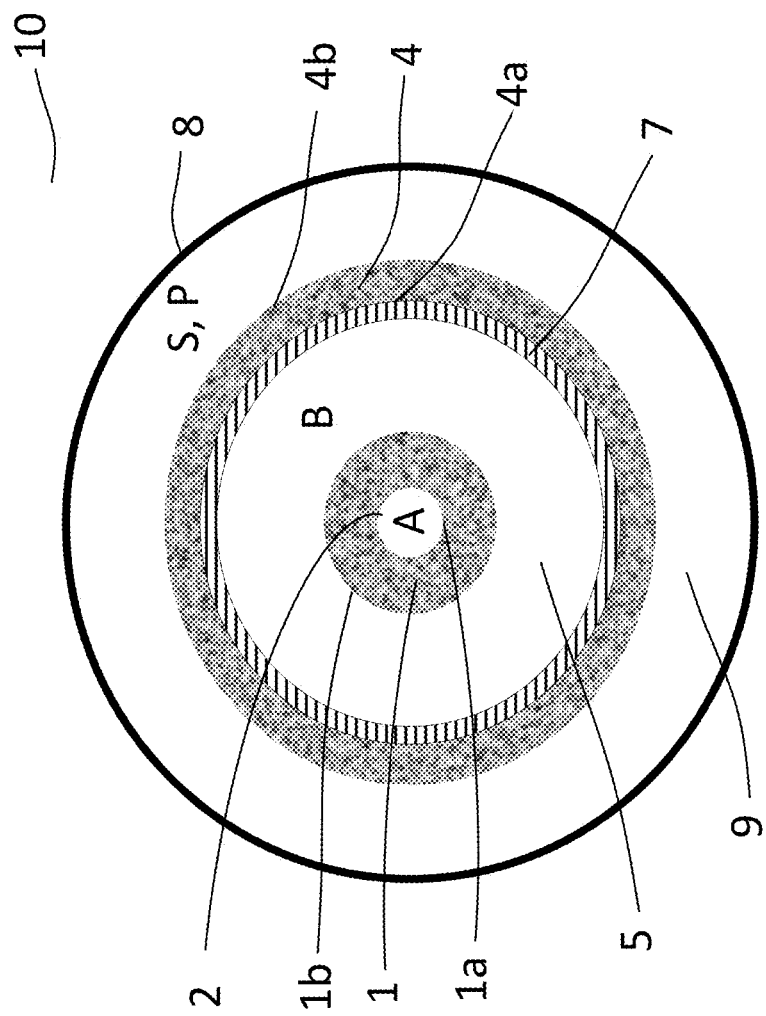
FIG. 6 depicts a transverse cross-sectional view of the first embodiment of this invention pictured in FIG. 5.

With reference to FIGS. 5 and 6, a first embodiment 10 of the reactor of this invention is illustrated in longitudinal and transverse cross-sections, respectively. The reactor 10 comprises an inner tube 1 comprised of a permeable material having an inner surface 1a and an outer surface 1b and further having a plurality of pores or channels extending from the inner surface 1a to the outer surface 1b. An inlet is provided at one end of the inner tube 1 for feeding a flow of a first reactant (A) into a first flow passage 2 defined by the inner surface 1a of inner tube 1. The opposite end 3 of the inner tube 1 may be open or sealed; and when sealed does not allow an exit for the flow. At least a portion of the flow of first reactant A proceeds through the pore structure from the inner surface 1a to the outer surface 1b, more suitably, at a controlled and uniform flow rate along the length of inner tube 1. Positioned circumferentially and coaxially around inner tube 1 is second tube 4, also constructed of a permeable material having an inner surface 4a and an outer surface 4b and further having a plurality of pores or channels extending from the inner surface 4a to the outer surface 4b. A first annular space between the outer surface 1b of inner tube 1 and the inner surface 4a of second tube 4 defines a second flow passage 5. The second flow passage 5 is hollow and essentially unobstructed space, meaning that essentially no solid particulates in the form of catalyst or catalyst support are present in or fill the volume. An inlet is provided at one end of second tube 4 for feeding a second reactant B. At its opposite end 6, second tube 4 may be open or sealed; and if sealed does not permit any flow to exit. A coating of catalyst 7 is provided along at least a portion of inner surface 4a of second tube 4. Mixing of reactants A and B occurs in second flow passage 5 defined by the annular space between the outer surface 1b of inner tube 1 and the inner surface 4a of second tube 4. Reaction occurs between reactants A and B on the surface of the catalyst 7; and reactants and products immediately pass through the permeable material of second tube 4 leaving the catalytic region, desirably at a controlled and uniform flow rate. A third tube 8, constructed from a non-permeable material lacking a permeable structure, is positioned circumferentially and coaxially around second tube 4. Third tube 8 has in inner surface 8a and an outer surface 8b. In this first embodiment of the invention, a second annular region defined by outer surface 4b of second tube 4 and inner surface 8a of third tube 8 is hollow and essentially unobstructed, meaning that it does not contain any particulate solid or structure in the form of catalyst, catalyst support, or heat transfer medium. An inlet is positioned at one end of third tube 8 for feeding a flow of a diluent or sweep fluid into a third flow passage 9; and an outlet 11 is positioned preferably at an opposite end of third tube 11 for exiting a flow of product mixture comprising a target product P, any unconverted reactants A and B, and any optional diluent and/or sweep fluid.

In this invention, overly-reactive reactant A, which is prone to secondary reactions with itself or with one or more reaction products P, is fed into the permeable inner tube 1, through flow passage 2, which restricts and controls the flow of reactant A into the second flow passage 5 (first annular region defined by outer surface 1b of inner tube 1 and inner surface 4a of second tube 4). The flow into passage 2 of overly reactive reactant A can be diluted with reactant B or any other diluent or sweep fluid, if desired. In contrast, reactant B is primarily fed directly into the annular region of flow passage 5. While the fluid fed into flow passage 5 can include a diluent or sweep fluid, the fluid fed directly into passage 5 excludes a flow of overly reactive reactant A. Subsequently, reactant A entering passage 5 through permeable tube 1 diffuses through a flow of reactant B in said annular region, essentially at controlled low dilution and essentially without reaction, until both B and A contact the catalyst 7 supported along a portion of the inner surface 4a of second tube 4. Upon contacting the catalyst, A and B react to form desired target product P. The resulting product mixture comprising target product P and any unconverted reactants A and B pass through the permeable pores or channel structure of second tube 4 into third flow passage 9 (second annular region defined by outer surface 4b of second tube 4 and the inner surface 8a of third tube 8). The resulting product stream comprising desired product P and any unconverted reactants A and B is swept into diluent or sweep fluid S flowing through the third flow passage 9. Since the concentration of high reactivity reactant A is controlled at the permeable inner tube 1, and since the concentration of target product P and unconverted reactants (A, B) are removed from the catalytic reaction zone 7 via the permeable second tube 4, the concentration of A as well as secondary reactions of A with itself or with product P to yield undesirable byproducts are greatly reduced. In FIG. 5, the flows of reactant A in inner tube 1, and reactant B in second tube 4, and diluent or fluid S in third tube 8 are aligned concurrently; that is, all flows move in parallel in the same axial direction.

As a practical example, A can represent overly reactive oxygen and B can represent methane; where the catalytic reaction of oxygen with methane yields the selective oxidation product methanol. The apparatus of the invention controls the flow of oxygen to the catalytic reaction zone (coating on the inner wall of the second tube 4), thereby diluting the concentration of oxygen and effectively reacting essentially all of the oxygen at the catalyst 7. The product mixture comprising the desired product methanol and any unconverted methane immediately exits the reactor through the permeable second tube 4 and third flow passage 9, essentially avoiding any of rapid secondary reactions of oxygen with methanol to yield undesirable byproducts, such as formaldehyde, formic acid, and carbon dioxide.

As another practical example, A can represent an overly reactive olefin, such as butylene, and B can represent an alkane, such as isobutane; wherein the catalytic reaction of butylene and isobutane yields the target alkylation product isooctane. The apparatus of the invention controls the flow of butylene to the catalytic reaction zone (coating on the inner wall of the second tube 4), thereby diluting the concentration of butylene and effectively reacting essentially all of the butylene at the catalyst 7. A product mixture comprising the desired isooctane product and unconverted isobutane immediately exits the reactor through permeable second tube 4, essentially avoiding any of the known secondary reactions of butylene with itself (self-polymerization) or with isooctane (further alkylation) to undesirable olefinic polymers and higher homologues of isooctane.

In yet another practical example, A can represent oxygen, and B can represent an alkane, such as methane; wherein the catalytic reaction of methane and oxygen yield ethylene via oxidative dehydrogenation of methane. The apparatus of the invention controls the flow of oxygen, or a fluid containing oxygen, air for example, to the catalytic reaction zone (coating on the inner wall of the second tube 4), thereby diluting the concentration of oxygen and effective reaction of oxygen at the catalyst 7. A product mixture comprising the desired ethylene product and unconverted methane immediately exits the reactor through permeable second tube 4, essentially avoiding complete oxidation of reactant methane or product ethylene. The product mixture comprising ethylene and unreacted methane can be further processed in subsequent reactive or non-reactive steps by means well known in the art. Additionally or optionally, excess methane can be separated from the product effluent and recycled into the second flow passage at the entrance of the reactor.

In terms of materials of construction, any of the inlets and outlets described in the apparatus of the invention can be obtained commercially from a large variety of mass flow control valves, injectors, nozzles, atomizers, and the like available in the market place. The actual design and materials of construction will depend upon the selected chemical reactants and products and the selected process conditions to which the apparatus will be subjected.

The first and second permeable walls, such as inner tube 1 and second tube 4 of FIG. 5, can be constructed from any permeable material that can withstand the temperature of the reaction process and the chemical environment to which the tubes are exposed. Suitable permeable materials include, without limitation, all permeable varieties of glasses, quartz, ceramics, metals, metal alloys, plastics, and carbon, wherein the aforementioned materials have been fabricated, etched, drilled, sintered, or otherwise penetrated so as to form a plurality of pores or channels capable of passing through liquids and gases. Preferred among these materials are alumina, aluminum, carbon, and alloys containing copper, aluminum, iron, and/or nickel. Other permeable materials include crystalline and non-crystalline size-selective materials, such as molecular sieves and zeolites and mesoporous materials designed to exclude one chemical from another or a mixture, based upon polarity or acidity. Non-limiting examples of size-selective materials include aluminosilicates, aluminosilicophosphates, zeolites, such as X, Y, beta, mordenite, and ZSM-5, mesoporous materials, such as MCM-41, and anion and/or cation modified versions thereof. Other permeable materials include solid ionic conductive materials, such as those well known for separating hydrogen or oxygen from a mixture including polymer electrolyte membrane (PEM) materials and solid oxide fuel cell (SOFC) materials as used in solid oxide fuel cells. Non-limiting examples of suitable solid ionic conductive materials include fluoropolymers, such as Nafion® brand fluoropolymers and variations thereof, as well as yttrium, scandium, or gadolinium stabilized or doped zirconia, lanthanum strontium manganate, and materials characterized by defect perovskite or pyrochlore structures.

It is important to note that the first permeable wall is essentially inert towards any chemical process and merely exists to pass through the overly reactive reactant in a controlled and uniform manner. In contrast, insofar as the second permeable wall contains a catalyst on its inner surface, the second permeable wall is catalytically active towards the desired chemical process. Additionally, the second permeable wall may contain a different catalyst located within its body or closer to its outer wall so as to catalyze a second desired chemical process.

The non-permeable wall, such as third tube 8, can be constructed from any non-permeable material that can withstand the temperature and chemical environment of the reaction process to which the third tube is exposed. Suitable materials include, without limitation, glass, quartz, ceramics, metals, and plastics that have essentially no measurable degree of permeability. Notably, it is possible to construct the entire reactor apparatus or portions of the apparatus via single or multiple material additive manufacturing.

The first flow passage is bounded by at least a portion of the inner surface of the first permeable wall, other constraining walls being employed as needed to define the first flow passage. The second flow passage is bounded by at least a portion of the outer surface of the first permeable wall and by the inner surface of the second permeable wall, other constraining walls being employed as needed to define the second flow passage. The third flow passage is bounded by at least a portion of the outer surface of the second permeable wall and the inner surface of the non-permeable wall, other constraining walls being employed as needed to define the third flow passage. As may be needed, other constraining walls are constructed typically from any of the aforementioned non-permeable materials.

The distance from the first permeable wall to the second permeable wall, for example, the annular distance from the outer surface 1b of permeable inner tube 1 to the inner surface 4a of permeable second tube 4 on FIGS. 5 and 6, is an important feature of this invention. This distance, together with flow rates of reactants A and B and temperature of operation, determines the concentration of overly reactive reactant A at the catalyst, relative to concentration of reactant B. Generally, one aims for a concentration ratio of B to A at the catalyst ranging from 50:1 to 1,000:1, preferably, from 200:1 to 750:1. More suitably, a ratio of diameter of permeable second tube 4, measured at surface 4a, to diameter of permeable inner tube 1, measured at surface 1b, ranges from greater than about 1.1:1 to less than about 20:1, preferred between about 1.25:1 and about 10:1, more preferred from about 1.5:1 to about 4:1.

The distance from the permeable second wall to the non-permeable third wall, for example, from outer surface 4b of permeable second tube 4 to inner surface 8a of non-permeable third tube 8 in FIGS. 5 and 6, can be any distance that sweeps the product stream away from the catalyst sufficiently quickly, so as to avoid undesirable secondary reactions at the catalyst 7. Such distance depends upon the scale of the reactor. A suitable ratio of diameter of non-permeable third tube 8, at surface 8a, to diameter of permeable second tube 4, at surface 4b, ranges from greater than about 1.1:1 to less than about 20:1, preferred between about 1.25:1 and about 10:1, more preferred from about 1.5:1 to about 4:1. Computer software, such as ANSYS Fluent, COMSOL, or CHEMKIN-Pro, can be used to provide guidance in selecting dimensions including tube diameters and lengths of permeable and non-permeable wall construction.

Diffusion due to concentration gradients is described in Chapter 11 of "The Properties of Gases and Liquids," $5^{th}$ edition, by Poling et. al. published by McGraw Hill, 2001; Chapter 11 being incorporated herein by reference. A concentration gradient and values of achievable concentration at a specific location are controlled by a combination of initial concentration, distance of diffusion, and diffusion coefficients, the latter being functions of molecular properties, temperature, and pressure. Thus, for a given overly reactive reactant, the choice of distance between the first permeable wall (outer surface 1b of permeable inner tube 1) and the catalyst coating supported on the second permeable wall (inner surface 4a at the second permeable tube 4) as well as selected operating conditions will determine the achievable concentration of the overly reactive reactant at the catalyst surface. Moreover in the presence of a flowing diluent, some transport due to bulk flow will occur additionally impacting achievable concentrations at the catalyst surface. The term "concentration at the catalyst surface" is meant to refer to a volumetric concentration of a fluid component measured at the catalyst surface. In the embodiment of this invention wherein the first and second flows are contained such that all of the flows must pass through a permeable surface, the effects of transport due to bulk flow are nearly eliminated, thereby advantageously preventing secondary reactions and build up of products in the second flow passage.

Another feature of this invention provides for controlled reaction rates. As reaction rate is proportional to concentration, control of a specific reactant concentration provides a means of controlling the corresponding reaction rate(s) of that specific reactant. For example, concentration of a reactant Fluid A mixed with co-reactant Fluid B in the catalyst volume is controlled by how A is mixed with B. In this invention, A must flow through a permeable wall to mix with B. Increasing or decreasing factors such as porosity of the permeable wall, temperature in the permeable wall, or force acting on fluid A will change the rate at which A enters B. Specifically, increasing the size of the pores or channels in the permeable wall increases the flow rate of Fluid A; whereas decreasing the size of the pores or channels in the permeable wall decreases the flow rate of Fluid A. Increasing pressure force on Fluid A, relative to Fluid B, increases the flow rate of A through the permeable wall. And generally, an increase in temperature reduces the viscosity of a fluid; in which case increasing the temperature of A increases the flow rate of A through the permeable wall. General guidance on controlling reaction rates through control of reactant concentrations can be found in the following engineering handbooks: "Chemical Reaction Engineering," $2^{nd}$ ed., by Octave Levenspiel, John Wiley & Sons, 1972; and "Transport Phenomena," by R. Byron Bird, Warren E. Stewart, and Edwin N. Lightfoot, John Wiley & Sons, 1960.

Once Fluid A enters Fluid B, Fluid A diffuses to the catalyst surface where the reaction of A with B takes place. Concentration of A as measured at the catalyst surface can be controlled by adjusting the physical properties of the flow system or by changing aspects of Fluid B. For example, increasing the distance between the first permeable wall and the catalyst surface will result in a reduced concentration of A at the catalyst surface, as the concentration gradient of A is a function of distance traveled. Changing Fluid B, for example, by reducing B viscosity via dilution with solvent or by increasing temperature, will reduce resistance to diffusion of A through Fluid B, and so increase the concentration of A at the catalyst surface.

Moreover, increasing the flow rate of Fluid B increases bulk transfer of A at the cost of reducing diffusive transfer of A to the catalyst surface. This means that as the flow rate of Fluid B is increased, more of A is carried downstream; and the concentration of A at the catalyst surface is reduced. Thus, controlling the flow rate of Fluid B is a convenient method of optimizing the concentration of A at the catalyst surface. If the flow rate of Fluid B is sufficient that some of Fluid A is swept past the distance represented by the first permeable wall in which A enters Fluid B, then additional lengths of catalyst and added length of second permeable wall 4 can be employed. By having the permeable wall of tube 4 longer than the permeable member of tube 1, Fluid A, whether reaching the catalyst surface by diffusive transport, bulk transport, or a combination of diffusive and bulk transport, will have the opportunity to completely react by having sufficient catalyst present.

The catalyst is preferably provided as a coating covering at least a portion of the inner surface of the second permeable wall (inner surface 4a of second tube 4, FIGS. 5 and 6). This invention does not, however, exclude the catalyst covering the surface or penetrating the pores and channel structure of the second permeable wall. Ideally, the catalyst is more concentrated on the inner surface, so as to reduce continuation of undesirable secondary reaction processes. The catalyst itself comprises any material capable of facilitating the desired reaction between reactants A and B, either in terms of increasing rate of reaction, or increasing conversion of reactants, or in terms of increasing selectivity to the desired target product. In oxidation and oxidative dehydrogenation processes, wherein oxygen is employed as the reactant, non-limiting examples of conventional oxidation catalysts include any metal or metal oxide associated with Groups IIIA, IVA, VA, VIA, VIIA, VIII, IB, and IIB of the Periodic Table of Elements. For alkylation processes, non-limiting examples of conventional alkylation catalysts include acid-modified zeolites and mesoporous materials, as well as solid acids and supported acids. The catalyst can comprise a single chemical element or chemical compound or a mixture of chemical elements and chemical compounds, as known in the art. The catalyst can also be supported on any known catalyst support, such as a refractory oxide, provided that the flow of reactants and products through the support is unhindered. In other words, the catalyst and any support associated therewith must also be permeable, consistent with the second permeable wall. The quantity of catalyst provided will depend upon the scale of the reactor, including the area of the inner surface of the second permeable wall. The skilled person will know how much catalyst is needed to provide for an acceptable conversion and yield of desired product.

In one embodiment the catalyst is provided as a coating on the inner surface of the second permeable wall. Accordingly, the catalyst can be deposited onto a washcoat on said inner surface, or deposited directly onto said inner surface as a combination catalyst-washcoat or as a catalyzed coating without a washcoat. If used, the washcoat can be applied by means commonly employed in the industry, such as dipping, or a flow-through "water-fall" method, or by vacuum pulling of an appropriate slurry followed by vacuum removal of excess slurry; with or without change in orientation of the part to be coated; or by gel injection followed by gel collapse onto the wall; or by spray coating or plasma deposition. Parts of the inner surface of the second permeable wall can be masked to avoid excess coating or coating in regions where catalyst is unwanted, such masking being effected by wax deposition or other means, in which case the wax is melted or burned off in a subsequent operation. After catalyst deposition the catalyst and, if present, the washcoat can be fixed via heat treating in oxidizing or reducing conditions as dictated by the type of catalyst and the specific chemical process to be employed. The skilled artisan knows of such methods. Whatever method is used, the permeability of the catalyst and second permeable wall are desirably maintained such that the overall permeability is the sum of the permeabilities of the catalyst and the wall.

Other methods of placing the catalyst onto the inner surface of the second permeable wall involve use of permeable inserts, in which case a catalyst is placed onto a pliable material by such means as wall coating or otherwise; and then the pliable material is formed into a shape suitable to conform to the inner surface of the second permeable wall and then positioned therein. One such configuration involves making a tube of conformable material, such as thin paper, ceramic paper, or flexible ceramic sheets, then coating it with catalyst, and then inserting it and fixing it onto the inner surface of the second permeable wall. Note that multiple catalysts and coatings can be applied to the inner surface of the second permeable wall; and the thickness, concentration, and/or activity of the catalyst can be adjusted so as to provide for varying catalyst performance for the chemical reaction of interest. If desired, different catalysts can be applied in different regions of the inner surface of the second permeable wall.

Figure 7:
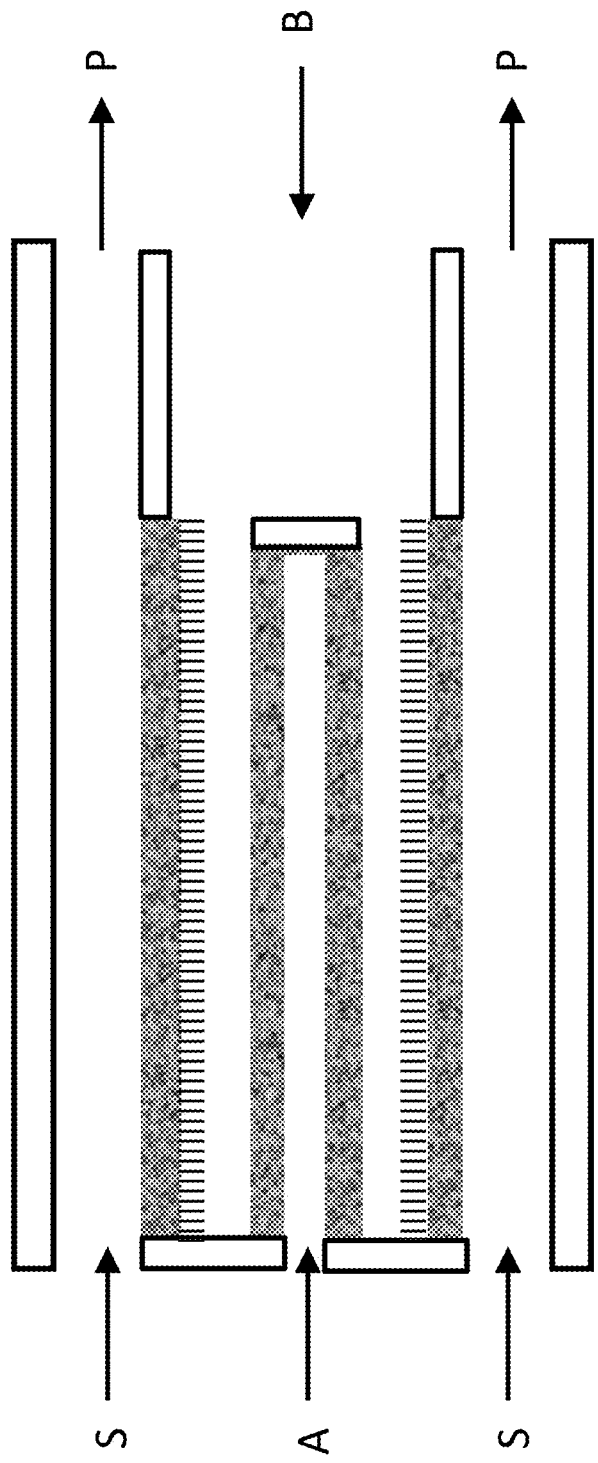
FIG. 7 depicts a longitudinal cross-sectional view of a second embodiment of a reactor of this invention.

As mentioned hereinabove, FIG. 5 illustrates the flows of reactants A and B, product P, and sweep fluid S in co-current flow. All inlet ports are on the same end of the reactor. In contrast, FIG. 7 illustrates another embodiment of the apparatus of this invention wherein inlets for reactant A and sweep fluid S are positioned at one end of the reactor; while the inlet for reactant B and the outlet for product P are positioned at the opposite end of the reactor. In this embodiment, the flows of A and S are cocurrent and in the same direction as the flow of P; but the flow of reactant B is countercurrent to the flows of A, S, and P. Otherwise, the permeable first and second tubes and the non-permeable third tube and their relationship to each other are similar to that shown in FIG. 5.

Figure 8:
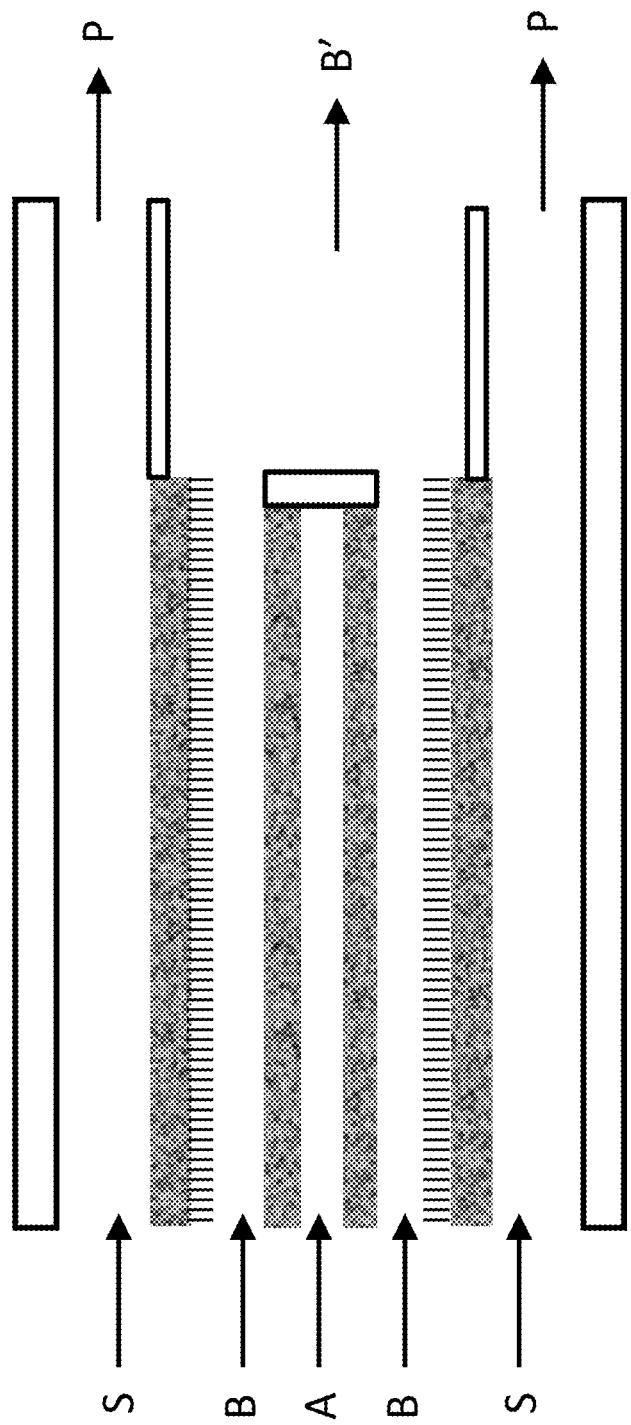
FIG. 8 depicts a longitudinal cross-sectional view of a third embodiment of a reactor of this invention.

In another embodiment of the invention, as shown in FIG. 8, all of the inlets for reactant A, reactant B, and sweep fluid S are positioned at one end of the reactor; and all flows of A, B, and S are cocurrent to each other. An exit for product P and any unconverted reactants exiting the third flow passage (annular region defined by outer surface 4b of second tube 4 and inner surface 8a of third tube 8) is positioned at the opposite end of the reactor. In FIG. 8, however, second tube 4 remains open-ended and allows for a portion of flow of reactant B from inlet to an exit of the second flow passage (annular region defined by outer surface 1b of first tube 1 and inner surface 4a of second tube 4).

Figure 9:
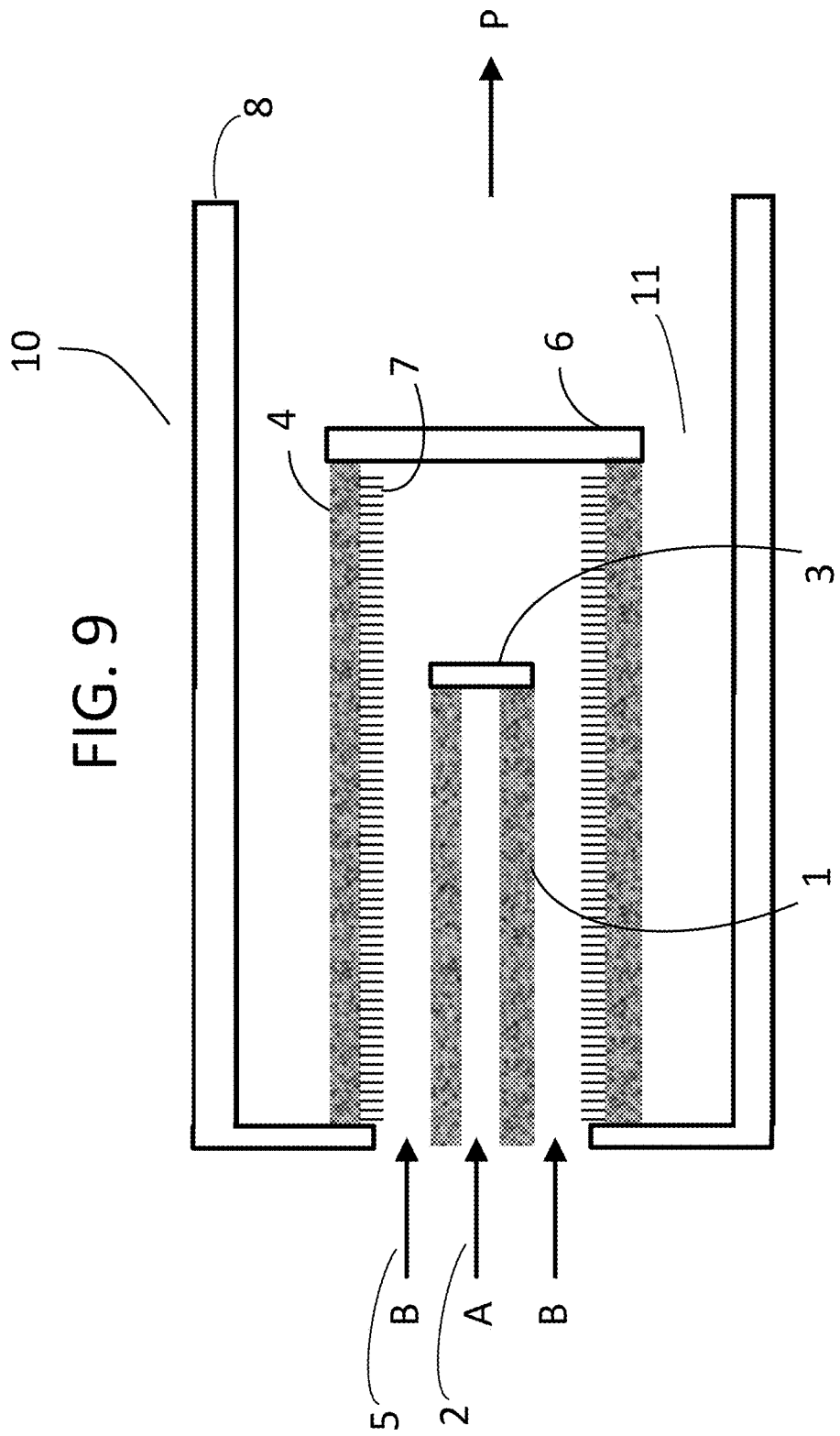
FIG. 9 depicts a longitudinal cross-sectional view of a fourth embodiment of a reactor of this invention.

In yet another embodiment as shown in FIG. 9, the inlet for sweep fluid S is eliminated. Rather, said third flow passage is capped at the inlet end. The reaction mixture comprising product P and any unconverted reactants A and B pass through the second permeable wall 4 and exit the reactor via the third flow passage.

With reference to FIG. 10, as another alternative, the inner surface 8a of non-permeable tube 8 can be coated with a catalyst 12 for further conversion of reactant A, or for removing side products, or for providing conversion of target product P into another product P' as in a multi-step synthesis. The catalyst coating 12 on inner surface 8a of the non-permeable wall 8 may be the same or different from the catalyst coating 7 on the inner surface of the second permeable wall 4.

In yet another embodiment of the invention, as shown in FIG. 11, the third flow passage, defined by the outer surface of the second permeable wall 4b and the inner surface of the non-permeable wall 8a, can be filled with a heat transfer medium 13. The heat transfer medium comprises any volume-filling material that allows for heat conduction from one surface to another while allowing for fluid passage throughout. Such configurations of volume-filling material and flow passages can be considered a 3-dimensional interpenetrating network. Examples of heat transfer media include foams and sponge-like materials, randomly packed wires, woven or non-woven screens, and wall-flow monolithic honeycombs, all of varying densities and proportions of fluid flow to solid volumes. In some cases, fluid flow may be in one direction only, while heat conduction can occur in three dimensions. In other cases, both fluid and heat flows are in all directions. For a packing consisting of screens, flow can enter and exit in several directions, such as simultaneously from an upstream to a downstream portion and through a permeable bounding surface; while sufficient mesh material is in contact with the permeable surface and other surfaces so as to permit effective heat transfer via conduction between surfaces and convective to the fluid flow.

In yet another embodiment of the invention, as shown in FIG. 12, a heat transfer module 14 containing a heat transfer medium is disposed circumferentially around the non-permeable wall, i.e., third tube 8. A heat transfer medium H fills the annular space defined by outer surface 8b of non-permeable third tube 8 and an inner surface of the heat transfer module 14. The heat transfer medium H can comprise any of those heat transfer media mentioned hereinbefore.

Figure 14:
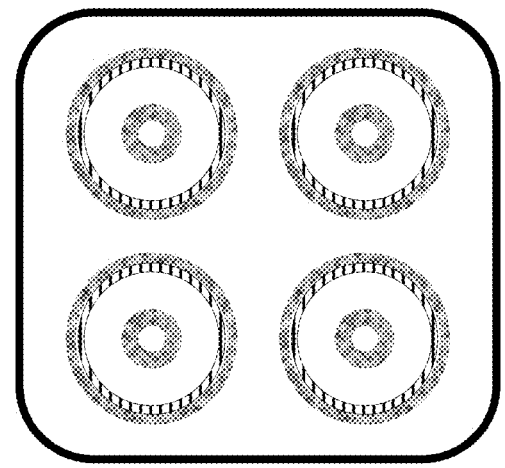
FIG. 14 depicts a transverse cross-sectional view of a second embodiment of a macro-reactor comprised of a plurality of micro-reactor embodiments of this invention.
Figure 15:
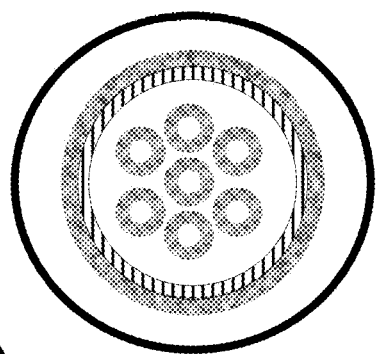
FIG. 15 depicts a transverse cross-sectional view of a third embodiment of a macro-reactor comprised of a plurality of micro-reactor embodiments of this invention.
Figure 13:
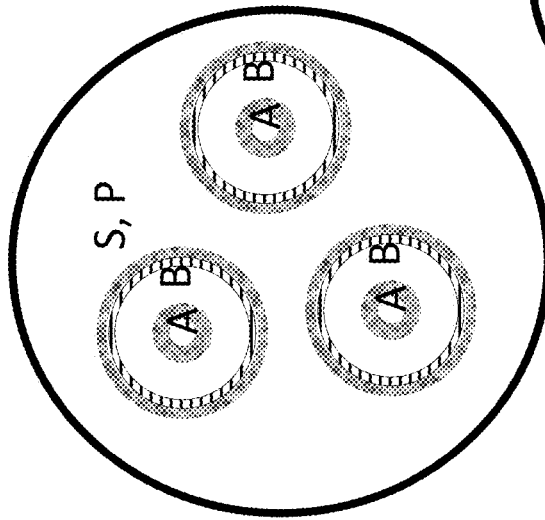
FIG. 13 depicts a transverse cross-sectional view of a first embodiment of a macro-reactor comprised of a plurality of micro-reactor embodiments of this invention.

FIGS. 13, 14, and 15 illustrate various alternative embodiments of the invention, wherein a plurality of micro-reactors are configured in accordance with this invention and bundled together within a macro-reactor.

Other embodiments of this invention, while not limiting, include configurations in which planes, planar channels or sheets, whether macro-, meso-, or microscopic, instead of tubes, are used to separate the flows, the aforementioned configurations incorporating porous or permeable walls in order to accomplish the goals of this invention. Multiple inlets and outlets can be employed. Other non-linear configurations can also be employed, such as spiral layering of tubes or layers, or concentric spheres or hemispheres. Alternatively, reverse flow configurations can be conceived in which under operative conditions the less reactive component diffuses through the more highly reactive component.

Figure 16:
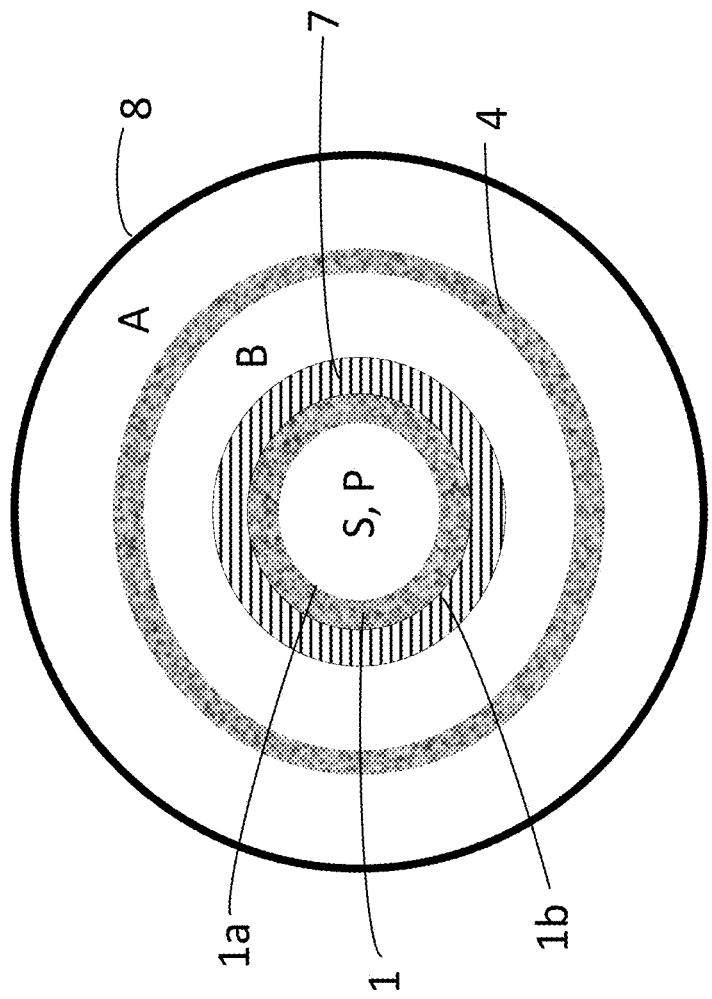
FIG. 16 depicts a transverse cross-sectional view of an embodiment of the invention wherein an apparatus similar to that shown in FIG. 5 is designed for operation in reverse mode.

FIG. 16, for example, illustrates an embodiment of this invention wherein the reactor of FIG. 5 is constructed to operate in reverse flow mode. Note that in FIG. 5, the first flow passage comprises the inner tube of first permeable wall 1, which receives the flow of overly reactive reactant A. The catalyst is supported on the inner surface 4a of the second permeable wall 4; and the third flow passage for exiting the fluid product mixture comprises the annular region between the second (permeable) and third (non-permeable) tubes, respectively, tubes 4 and 8. In contrast, FIG. 16 illustrates a reverse flow design. Here, the tubular structure is similar to that shown in FIG. 5, but now the catalyst 7 is supported on the outer surface 1b of the inner tube 1. The first flow passage for reactant A comprises the annular region between the second permeable tube 4 and the outer non-permeable tube 8. The flow passage for reactant B is the annular region between the first permeable tube 1 and the second permeable tube 4. The flow passage for exiting the fluid product mixture comprises the passage bounded by the inner permeable tube 1.

EMBODIMENTS

Example 1

In the reaction of isobutane ($iC_4$) with cis-2-butene ($C_4^=$) to form a mixture of isooctane isomers ($C_8H_{18}$), undesired reactions can occur, such as cis-2-butene self reaction to form unsaturated octene isomers $C_8H_{16}$ ($C_8^=$), or reactions of isooctane with cis-2-butene to form dodecane isomers $C_{12}H_{26}$ ($iC_{12}$). The most prevalent undesired reactions have reaction stoichiometry and reaction rates that can be given by:

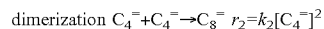

dimerization $C_4^= + C_4^= \rightarrow C_8^=$  $r_2 = k_2 [C_4^=]^2$

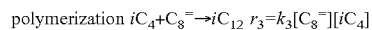

polymerization $iC_4 + C_8^= \rightarrow iC_{12}$  $r_3 = k_3 [C_8^=][iC_4]$

A reactor of this invention is constructed from a nest of three concentric cylindrical tubes according to the design illustrated in FIG. 9. The reactor comprises an inner tube 1 constructed of porous stainless steel (Mott Corporation, Farmington, Conn.) having an outer diameter of 0.25 inch (0.64 cm), an inner diameter of 0.125 inch (0.32 cm), an average porosity of 0.5 microns, a percent porosity of 35 percent, and a porous length of 4 inches (10.2 cm). The reactor further comprises a second porous stainless steel tube 4 (Mott Corporation, Farmington, Conn.) having an inside diameter of 0.55 inch (1.40 cm), an outer diameter of 0.625 inch (1.59 cm), an average porosity of 0.5 microns, a percent porosity of 35 percent, and a porous length of 6 inches (15.2 cm). The second tube has a catalyst coating applied to its inner surface covering the porous section. In this example, the catalyst (1.7 g) is ZSM-5 zeolite. Each porous tube is attached via butt-welds to a nonporous inlet section to allow for a flow of reactant independently into each tube. At the end opposite the inlets, each tube is terminated with a plug (3, 6), so that flows 2 and 5 pass respectively through the porous sections 1 and 4 uniformly along each tube. An outer tube 8, having an inner diameter of 0.875 inch (2.22 cm) and an outer diameter of 1.0 inch (2.54 cm), constructed of a nonporous stainless steel, provides for an annular outlet passage 11 from the reactor.

A mixture "Fluid A" is prepared consisting of 50 mole percent cis-2-butene and 50 mole percent isobutane. "Fluid B" is 100 percent isobutane. Fluid A is fed into the first flow passage 2 of inner tube 1. Fluid B is fed into flow passage 5, the annular region bounded by inner tube 1 and second tube 4. The flow rate of Fluid B is 50 percent greater than the sum flow of Fluid A, so that the overall molar ratio of isobutane to cis-2-butene is 4:1. Fluid A is fed to the inner tube 1 to provide an isobutane flow rate of 0.00048 mol/min (28 mg/min) and a cis-2-butene flow rate of 0.00048 mol/min (28 mg/min). Fluid B, isobutane, is fed to the annular region to provide a flow rate of 0.00145 mol/min (84 mg/min). The average concentration of cis-2-butene at the catalyst surface is 0.2 mole percent over the length of the catalyst coating the porous section of tube 4. At 520 psia (3.6 MPa) and 167° C., the conversion of cis-2-butene is 60 mole percent. The average concentration of each fluid component with respect to length along the reactor, as measured at the catalyst surface, is shown in Table 1.

TABLE 1

Isobutane Alkylation, Average Concentrations Along Length of Reactor, as measured at Catalyst Surface

|  | Isobutane mole % | cis-2-butene mole % | Isooctane mole % |
| --- | --- | --- | --- |
| Example 1 (FIG. 9) | 99.8 | 0.14 | 0.06 |
| CE-1 (FIG. 1) | 78.6 | 14.5 | 6.8 |
| CE-2 (FIG. 4) | 92.7 | 0.14 | 7.1 |

Comparative Experiment 1 (CE-1)

For comparative purposes, a prior art fixed bed reactor illustrative of FIG. 1 is constructed from a single cylindrical tube to yield the same isobutene ($C_4^=$) conversion as in Example 1. A ZSM-5 catalyst is provided as particles of 1/16 inch (1.59 mm) diameter, which fill the volume of the tube. The reactor receives a fully mixed combined stream of a 4:1 mole ratio of isobutane and cis-2-butene. Operational conditions of temperature and pressure are similar to those used in Example 1. Table 1 lists average concentrations of isobutane and cis-2-butene reactants and isooctane product along the length of the reactor.

When Comparative Experiment 1 is compared with Example 1, it is seen that when operated to the same cis-2-butene conversion, the fixed bed reactor of the prior art provides for significantly higher concentrations of cis-2-butene and isooctane, as compared with the reactor and process of this invention. Accordingly, the opportunity for undesirable self-polymerization of cis-2-butene and undesirable reaction of cis-2-butene with the product isooctane is considerably reduced in the reactor of the invention.

Comparative Experiment 2 (CE-2)

For comparative purposes, a prior art reactor is constructed in accordance with US 2008/0245682A1, as represented by FIG. 4 herein, wherein an inner porous tube is positioned within an outer non-permeable tube. The reactor has the same length as the reactor of Example 1. The catalyst composition and operational conditions are identical to those used in Example 1, except that the catalyst is provided as a coating along the inner surface of the non-permeable outer tube. Cis-2-butene mixed 1:1 with isobutane flows as reactant "A" into the inner tube and through its porous wall; isobutane flows as reactant "B" through the annular volume between the inner and outer tubes. The reactants contact the catalyst on the surface of the non-permeable outer tube. Table 1 lists average concentrations of isobutane and cis-2-butene reactants and isooctane product along the length of the reactor. When Comparative Experiment 2 is compared with Example 1, it is seen that the prior art reactor of FIG. 4 provides for significantly higher concentration of isooctane, as compared with the reactor and process of this invention. Accordingly, the opportunity for undesirable reactions of cis-2-butene with the product isooctane is considerably reduced in the reactor of the invention.

Using the concentration data of Table 1, the ratios of reaction rates for dimerization and polymerization reactions of cis-2-butene, which at constant temperature are functions of concentrations only, are shown in Table 2.

TABLE 2

Comparison of Reaction Rates for Undesired Reactions

| | Ratio of Rates, dimerization | Ratio of Rates, polymerization |
|---|---|---|
| E-1/(CE-1) (Invention FIG. 9/Prior Art FIG. 1) | $9.3 \times 10^{-5}$ | $8.5 \times 10^{-5}$ |
| E-1/(CE-2) (Invention FIG. 9/Prior Art FIG. 4) | 1.0 | $8.4 \times 10^{-3}$ |

From Table 2 it is seen that the reactor and process of the invention (E-1, FIG. 9) forms significantly lower quantities of undesirable dimerization and polymerization products due to much lower reaction rates, as compared with the prior art fixed bed process (CE-1, FIG. 1). Also, the reactor and process of the invention (E-1, FIG. 9) forms a significantly lower quantity of undesirable polymerization products, as compared with the prior art reactor and process of Comparative Experiment 2 (CE-2, FIG. 4). The advantages of the invention derive from removal of the product from the catalyst area via permeable tube 4, so as to avoid build-up of side-products while the product stream leaves the reactor.

Example 2

The oxidation of methane with oxygen to form methanol is simulated in a reactor of this invention according to the embodiment illustrated in FIG. 9. (WARNING: While practice of the invention should not produce explosive mixtures of methanol and air, safety measures should be implemented.) Fluid A consists of 100 percent air. Fluid B consists of 100 percent methane. Fluid A is fed into the flow passage 2 of inner tube 1. Fluid B is fed into the flow passage 5 comprising the annular region between permeable tube 1 and permeable second tube 4. Air arrives uniformly from the starting point to the termination point of the catalyst coating applied to the inner surface of the permeable second tube 4, due to pressure build-up in passage 2 distributing the air flow uniformly along the permeable length of said passage.

The following reaction conditions are employed: a 16 inch (40.6 cm) long reactor using the same stainless steel porous tubes 2 and 4 as used in Example 1, with the exception that the entire length of tubes 2 and 4 are porous and that the catalyst (H-modified zeolite, 1.1 g) coats the entire inner surface of tube 4; a space velocity of 0.2 mol $CH_4$/gram-catalyst/hour; a flow rate of 0.083 standard liters per minute (SLPM) methane and a flow rate of 0.168 SLPM air; methane conversion 84.8 percent and oxygen conversion 100 percent.

FIG. 17 presents a graph of methane conversion as a function of relative distance along the length of the reactor. As seen, a methane conversion of over 80 mole percent is achieved using the apparatus of this invention. FIG. 20 illustrates a graph of methanol yield as a function of relative distance along the length of the reactor. As seen, a methanol yield of 80 mole percent is achieved using the apparatus of this invention.

FIG. 23 presents a graph of carbon dioxide concentration in the product stream as a function of relative distance along the reactor. As seen, the carbon dioxide concentration comprises only about 1 mole percent of the product stream when using the apparatus of this invention. FIG. 26 presents a graph of methanol concentration in the product stream as a function of relative distance along the reactor. As seen, the methanol concentration comprises 27 mole percent of the product stream when using the apparatus of this invention.

Comparative Experiment 3 (CE-3) (Simulation)

For comparative purposes, a simulation is provided illustrating the prior art as represented by a fixed bed reactor (FIG. 1). (WARNING: Hazardous explosive mixtures; simulation not intended for laboratory use.) The prior art fixed bed reactor illustrative of FIG. 1 is contemplated as having the same length as the reactor of Example 2. The catalyst is provided as particles of 1/16 inch (1.56 mm) diameter filling the reactor volume. Operational conditions of flow rates, temperature and pressure are otherwise similar to those used in Example 2. The reactor receives a fully mixed combined stream of methane and air.

FIG. 18 presents a graph of methane conversion as a function of relative distance along the length of the reactor. As seen, a methane conversion of 20 mole percent is achieved at which point the methane-air mixture enters an explosive regime, and the reaction must be quenched. FIG. 21 illustrates a graph of methanol yield as a function of relative distance along the length of the reactor. A methanol yield of only 20 mole percent is achieved, when the mixture enters the explosive regime. It is seen that the example of the invention E-2 provides for a significantly higher methane conversion and methanol yield as compared with CE-3.

FIG. 24 presents a graph of carbon dioxide concentration in the product stream as a function of relative distance along the length of the comparative reactor. As seen, the carbon dioxide concentration reaches only 1 percent when the reaction mixture enters the explosive regime. FIG. 27 presents a graph of methanol concentration in the product stream as a function of relative distance along the comparative reactor. As seen, the methanol concentration in the product stream is only about 8 percent, when the reaction must be quenched. By comparison, the methanol concentration in the product stream is significantly higher in example E-2 of the invention.

Comparative Experiment 4 (CE-4) (Simulation)

For comparative purposes, a simulation is provided to illustrate the prior art of US 2008/0234528A1, as represented by FIG. 4 herein. (WARNING: While practice of this comparative experiment should not produce explosive mixtures of methanol and air, nevertheless safety measures should be implemented.) The reactor is provided in the same length as the reactor of Example 2. The catalyst is provided as a coating on the wall of the outer tube, which is non-permeable. Fluid A consists of 100 percent air. Fluid B consists of 100 percent methane. Fluid A is fed into the flow passage of the permeable inner tube. Fluid B is fed into the flow passage of the annular region between the permeable inner tube and the non-permeable outer tube. Air is assumed to be fed uniformly from the starting point to the termination point of the catalyst coating applied to the inner surface of the outer tube. Operational conditions of flow rates, temperature and pressure are otherwise similar to those used in Example 2.

FIG. 19 presents a graph of methane conversion as a function of relative distance along the length of the reactor. As seen, a methane conversion of about 40 mole percent is achieved with this comparative apparatus. FIG. 22 illustrates a graph of methanol yield as a function of relative distance along the length of the reactor. As seen, a methanol yield of only 20 mole percent is achieved. By comparison, the methane conversion and methanol yield are significantly higher in the apparatus of this invention as illustrated in E-2.

FIG. 25 presents a graph of carbon dioxide concentration in the product stream as a function of relative distance along the reactor. As seen, the carbon dioxide concentration comprises about 40 mole percent of the product stream. FIG. 28 presents a graph of methanol concentration in the product stream as a function of relative distance along the reactor. As seen, the methanol concentration in the product stream is only about 8 mole percent. By comparison, the carbon dioxide production is significantly lower and methanol concentration is significantly higher in example E-2 of the invention.

Example 3

Methane is reacted with oxygen in an oxidative dehydrogenation process to form ethylene in a reactor of this invention as illustrated in FIG. 9. A non-permeable quartz tube (36 inches long×1.5 inches outer diameter) (91 cm×3.8 cm outer diameter), represented by tube 8 in FIG. 9, was placed centrally and horizontally inside a standard tube furnace (24 inch, 61 cm). An outer porous tube, represented by tube 4 in FIG. 9, constructed of porous alumina ceramic (Refractron, Newark, N.Y.) having an outer diameter of 25 mm, an inner diameter of 21 mm, an average pore diameter of 8 microns, and a percent porosity of 43 percent, was positioned within the non-permeable quartz tube. An outlet plug 6 was constructed from a machinable alumina ceramic (McMaster-Carr, Robbinsville, N.J.) and sealed to the end of tube 4 with zirconia paste. Referring to FIG. 9, an inner porous tube 1 constructed of porous alumina ceramic (Refractron, Newark, N.Y.) having an outer diameter of 13 mm, an inner diameter of 8 mm, an average pore diameter of 1 micron, and a porosity of 43 percent, was positioned within the outer porous tube 4. An 8 inch (20.3 cm) section of tube 1 was plugged at one end, 3, with zirconia paste (Cotronics Corp., Brooklyn, N.Y.).

'O'-ring fittings (Swagelok Company) were configured as flanges at both ends of tube 8 to allow for two separate inlet flow passages 5 and 2 and one outlet flow passage 11. At the end of tube 1 opposite plug 3, inner porous tube 1 was attached to a stainless steel inlet tube, with connections sealed against leakage by using zirconia paste, to allow for flow passage 2 to pass from one of the inlet flanges through the center of porous inner tube 1. As the end of tube 4 opposite plug 6, outer porous tube 4 was attached to a ceramic manifold and connections sealed against leakage with zirconia paste, so as to allow flow passage 5 to pass through the second inlet flange through the annular section between the inner wall of tube 4 and the outer wall of tube 1.

Catalyst, 7, was prepared by depositing a Mn—Na—W—Si oxide powder material into the pores of porous tube 4. The catalyst was synthesized in a two-step process. In a first step a manganese nitrate solution was added to fumed silica. The amount of nitrate in the solution was calculated such that the resulting content of Mn was 2 wt. percent based on weight of $SiO_2$. The resulting slurry was mixed for several hours then dried overnight at 130° C. In a second step a solution of $Na_2WO_4$ was added to the Mn-silica such that the resulting loading of tungstenate was 5 wt. percent based on weight of $SiO_2$. The resulting slurry was deposited onto the pores of the ceramic tube, which was then dried at 130° C. followed by air treatment at 900° C. for 8 hours. Sufficient catalyst was loaded onto tube 4 to give a final loading of 30 g catalyst per 4 inches (10.2 cm) of porous length.

Through flow passage 2 was passed a gas consisting of 21 vol. percent oxygen ($O_2$) and 79 vol. percent nitrogen ($N_2$) at 258 standard cubic centimeters per minute (SCCM). Through flow passage 5 was passed a gas mixture consisting of nitrogen (221 SCCM) and methane (268 SCCM). The reactor temperature was measured by a thermocouple touching the midpoint of outer tube 8 and controlled to achieve values of from 700° C. to 875° C. Reactor back-pressure was held at 1 atm. Product gas was dried to remove water, and the dried gas was analyzed for hydrogen ($H_2$), oxygen ($O_2$), nitrogen ($N_2$), methane ($CH_4$), carbon monoxide (CO), carbon dioxide ($CO_2$), ethylene ($C_2H_4$), ethane ($C_2H_6$), propylene ($C_3H_6$), and propane ($C_3H_8$) by gas chromatography (GC) analysis of gas taken from outlet fluid stream 11. $CH_4$ conversion was calculated by the equation: [1.00−($CH_4$ mole flow rate in outlet)/($CH_4$ mole flow rate in inlet)]. Selectivity to $C_2H_4$ was calculated by the ratio of carbon contained in ethylene divided by carbon contained in methane feed, in terms of mole flow rates: (C in $C_2H_4$)/(C in $CH_4$ feed). At 800° C., methane conversion was found to be 24.2 percent and selectivity to $C_2H_4$ was found to be 47.3 percent.

While the invention has been described in detail in connection with only a limited number of embodiments, it should be readily understood that the invention is not limited to such disclosed embodiments. Rather, the invention can be modified to incorporate any number of variations, alterations, substitutions or equivalent arrangements not heretofore described, but which are commensurate with the spirit and scope of the invention. Additionally, while various embodiments of the invention have been described, it is to be understood that aspects of the invention may include only some of the described embodiments. Accordingly, the invention is not to be seen as limited by the foregoing description, but is only limited by the scope of the appended claims.

The invention claimed is:

1. A process of forming a target chemical product, the process comprising:
   (a) feeding a first reactant into a first flow passage, wherein the first reactant is capable of reacting with itself or is capable of reacting with the target product in the presence of a catalyst, wherein said first reactant comprises oxygen;
   (b) passing the first reactant in the first flow passage through a first permeable wall into a second flow passage; the first permeable wall characterized by an inner surface and an outer surface and a plurality of pores extending from the inner surface to the outer surface thereof; the first permeable wall extending along at least a portion of length of the first flow passage and being fluidly connected thereto;
   (c) feeding a second reactant into the second flow passage extending along a length of the first permeable wall; the second flow passage being fluidly connected to the outer surface of the first permeable wall, wherein said second reactant comprises a $C_{1-10}$ hydrocarbon; wherein the first and second reactants mix within the second flow passage;
   (d) contacting the mixture of the first and second reactants on a catalyst supported on an inner surface of a second permeable wall, wherein the $C_{1-10}$ hydrocarbon is selectively oxidized to a $C_{1-10}$ alcohol; the second permeable wall characterized by the inner surface and an outer surface and a plurality of pores extending from the inner surface to the outer surface thereof; the second permeable wall extending along a length of the second flow passage and fluidly connected thereto;
   (e) passing the $C_{1-10}$ alcohol and any unconverted first and second reactants through the second permeable wall into a third flow passage extending along the length of the second permeable wall; the third flow passage being fluidly connected to the outer surface of the second permeable wall and bounded by a non-permeable wall;
   (f) exiting the $C_{1-10}$ alcohol and any unconverted first and second reactants through an outlet connected to the third flow passage.

2. The process of claim 1, wherein said second reactant comprises methane and wherein said methane is selectively oxidized to methanol; comprising:
   passing the methanol and any unconverted first and second reactants through the second permeable wall into the third flow passage extending along the length of the second permeable wall; the third flow passage being fluidly connected to the outer surface of the second permeable wall and bounded by the non-permeable wall; and
   exiting the methanol and any unconverted first and second reactants through the outlet connected to the third flow passage.

3. A process of forming a target chemical product, the process comprising:
   (a) feeding a first reactant into a first flow passage, wherein the first reactant is capable of reacting with itself or is capable of reacting with the target product in the presence of a catalyst, wherein said first reactant comprises a $C_{2-6}$ olefin;
   (b) passing the first reactant in the first flow passage through a first permeable wall into a second flow passage; the first permeable wall characterized by an inner surface and an outer surface and a plurality of pores extending from the inner surface to the outer surface thereof; the first permeable wall extending along at least a portion of length of the first flow passage and being fluidly connected thereto;
   (c) feeding a second reactant into the second flow passage extending along a length of the first permeable wall; the second flow passage being fluidly connected to the outer surface of the first permeable wall, wherein said second reactant comprises a $C_{2-10}$ alkane; wherein the first and second reactants mix within the second flow passage;
   (d) contacting the mixture of the first and second reactants on a catalyst supported on an inner surface of a second permeable wall, including selective alkylation of the $C_{2-10}$ alkane with the $C_{2-6}$ olefin to form a corresponding alkylated alkane; the second permeable wall characterized by the inner surface and an outer surface and a plurality of pores extending from the inner surface to the outer surface thereof; the second permeable wall extending along a length of the second flow passage and fluidly connected thereto;
   (e) passing the alkylated alkane and any unconverted first and second reactants through the second permeable wall into a third flow passage extending along the length of the second permeable wall; the third flow passage being fluidly connected to the outer surface of the second permeable wall and bounded by a non-permeable wall;
   (f) exiting the alkylated alkane and any unconverted first and second reactants through an outlet connected to the third flow passage.

4. The process of claim 3, wherein said first reactant comprises cis-2-butene and wherein said second reactant comprises isobutane, comprising:
   (d) contacting the mixture of the first and second reactants on the catalyst supported on an inner surface of the second permeable wall, including selective alkylation of the isobutane with the cis-2-butene to form isooctane; the second permeable wall characterized by the inner surface and the outer surface and the plurality of pores extending from the inner surface to the outer surface thereof; the second permeable wall extending along the length of the second flow passage and fluidly connected thereto;
   (e) passing the isooctane and any unconverted first and second reactants through the second permeable wall into the third flow passage extending along the length of the second permeable wall; the third flow passage being fluidly connected to the outer surface of the second permeable wall and bounded by the non-permeable wall;
   (f) exiting the isooctane and any unconverted first and second reactants through the outlet connected to the third flow passage.

5. A process of forming a target chemical product, the process comprising:
   (a) feeding a first reactant into a first flow passage, wherein the first reactant is capable of reacting with itself or is capable of reacting with the target product in the presence of a catalyst, wherein said first reactant comprises oxygen;

(b) passing the first reactant in the first flow passage through a first permeable wall into a second flow passage; the first permeable wall characterized by an inner surface and an outer surface and a plurality of pores extending from the inner surface to the outer surface thereof; the first permeable wall extending along at least a portion of length of the first flow passage and being fluidly connected thereto;

(c) feeding a second reactant into the second flow passage extending along a length of the first permeable wall; the second flow passage being fluidly connected to the outer surface of the first permeable wall, wherein said second reactant comprises a $C_{1-8}$ alkane; wherein the first and second reactants mix within the second flow passage;

(d) contacting the mixture of the first and second reactants on a catalyst supported on an inner surface of a second permeable wall, wherein the $C_{1-8}$ alkane is oxidatively dehydrogenated with the oxygen to form a $C_{2-9}$ alkene; the second permeable wall characterized by the inner surface and an outer surface and a plurality of pores extending from the inner surface to the outer surface thereof; the second permeable wall extending along a length of the second flow passage and fluidly connected thereto;

(e) passing the $C_{2-9}$ alkene and any unconverted first and second reactants through the second permeable wall into a third flow passage extending along the length of the second permeable wall; the third flow passage being fluidly connected to the outer surface of the second permeable wall and bounded by a non-permeable wall;

(f) exiting the $C_{2-9}$ alkene and any unconverted first and second reactants through an outlet connected to the third flow passage.

6. The process of claim 5, wherein said second reactant comprises methane; wherein the first and second reactants mix within the second flow passage; comprising:

(d) contacting the mixture of the first and second reactants on the catalyst supported on the inner surface of the second permeable wall, wherein the methane is oxidatively dehydrogenated with the oxygen to form ethylene; the second permeable wall characterized by the inner surface and the outer surface and the plurality of pores extending from the inner surface to the outer surface thereof; the second permeable wall extending along the length of the second flow passage and fluidly connected thereto;

(e) passing the ethylene and any unconverted first and second reactants through the second permeable wall into the third flow passage extending along the length of the second permeable wall; the third flow passage being fluidly connected to the outer surface of the second permeable wall and bounded by the non-permeable wall;

(f) exiting the ethylene and any unconverted first and second reactants through the outlet connected to the third flow passage.

* * * * *